US008852897B2

(12) United States Patent
Savrasova et al.

(10) Patent No.: US 8,852,897 B2
(45) Date of Patent: Oct. 7, 2014

(54) METHOD FOR PRODUCING AN L-AMINO ACID USING A BACTERIUM OF THE ENTEROBACTERIACEAE FAMILY

(71) Applicant: Ajinomoto Co., Inc., Tokyo (JP)

(72) Inventors: Ekaterina Alekseevna Savrasova, Moscow (RU); Natalia Viktorovna Stoynova, Moscow (RU); Gen Nonaka, Kanagawa (JP); Shunsuke Yamazaki, Kanagawa (JP); Kazuhiro Takumi, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/886,762

(22) Filed: May 3, 2013

(65) Prior Publication Data

US 2013/0224806 A1 Aug. 29, 2013

Related U.S. Application Data

(62) Division of application No. 13/004,188, filed on Jan. 11, 2011, now Pat. No. 8,460,903.

(30) Foreign Application Priority Data

Jan. 15, 2010 (RU) ................................ 2010101136

(51) Int. Cl.
*C12P 13/04* (2006.01)
*C12P 13/12* (2006.01)
*C12N 1/21* (2006.01)

(52) U.S. Cl.
USPC .......................... 435/106; 435/113; 435/252.3

(58) Field of Classification Search
USPC ...................................... 435/106, 113, 252.3
See application file for complete search history.

(56) References Cited

U.S. PATENT DOCUMENTS

| | | | |
|---|---|---|---|
| 4,278,765 A | 7/1981 | Debabov et al. | |
| 4,346,170 A | 8/1982 | Sano et al. | |
| 5,661,012 A | 8/1997 | Sano et al. | |
| 5,972,663 A | 10/1999 | Winterhalter et al. | |
| 6,040,160 A | 3/2000 | Kojima et al. | |
| 6,218,168 B1 * | 4/2001 | Leinfelder et al. | ......... 435/252.3 |
| 6,610,836 B1 | 8/2003 | Breton et al. | |
| 7,056,713 B1 | 6/2006 | Hershfield et al. | |
| 7,186,531 B2 | 3/2007 | Akhverdian et al. | |

(Continued)

FOREIGN PATENT DOCUMENTS

| | | |
|---|---|---|
| EP | 0 885 962 | 12/1998 |
| EP | 1382684 | 1/2004 |

(Continued)

OTHER PUBLICATIONS

Result 5, direct submission of De Maayer et al., Jan. 12, 2010, 100% seq. identity, search of SEQ ID No. 4 in GenEmbl DNA database, searched on Jun. 23, 2014.*

(Continued)

*Primary Examiner* — Rosanne Kosson
(74) *Attorney, Agent, or Firm* — Shelly Guest Cermak; Cermak Nakajima McGowan LLP

(57) ABSTRACT

A method for producing an L-amino acid is described using a bacterium of the Enterobacteriaceae family, wherein the bacterium contains a protein which is able to confer resistance to growth inhibition by L-cysteine.

18 Claims, 1 Drawing Sheet

(56) References Cited

U.S. PATENT DOCUMENTS

Figure 1A:
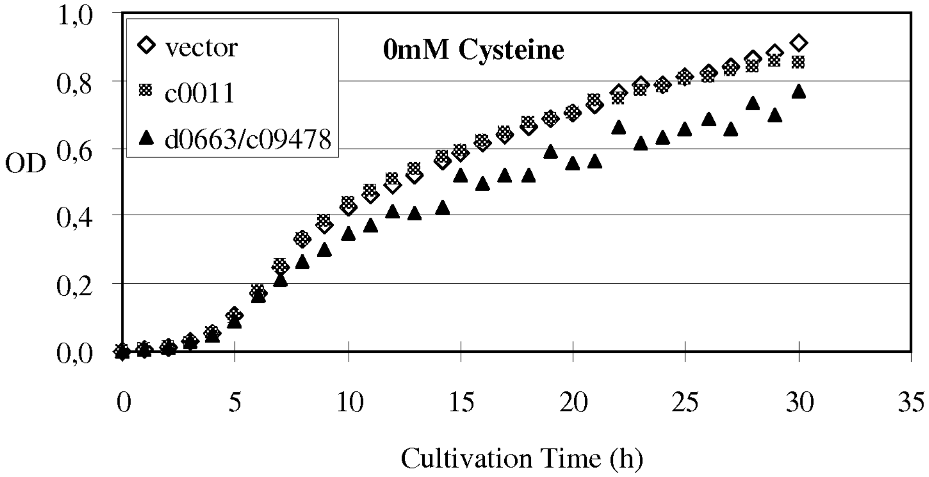

| | | | |
|---|---|---|---|
| 7,259,003 | B2 | 8/2007 | Livshits et al. |
| 7,470,531 | B2 | 12/2008 | Rehberger et al. |
| 7,531,332 | B2 | 5/2009 | Livshits et al. |
| 7,618,803 | B2 | 11/2009 | Tabolina et al. |
| 7,618,804 | B2 | 11/2009 | Tabolina et al. |
| 2005/0221453 | A1 | 10/2005 | Takagi et al. |
| 2005/0239177 | A1 | 10/2005 | Livshits et al. |
| 2006/0088919 | A1 | 4/2006 | Rybak et al. |
| 2008/0050784 | A1 | 2/2008 | Livshits et al. |
| 2009/0226983 | A1 | 9/2009 | Nonaka et al. |
| 2009/0226984 | A1 | 9/2009 | Nonaka et al. |
| 2010/0209977 | A1 | 8/2010 | Takumi et al. |
| 2010/0216196 | A1 | 8/2010 | Nonaka et al. |
| 2010/0233765 | A1 | 9/2010 | Nonaka et al. |
| 2011/0033902 | A1 | 2/2011 | Nonaka et al. |
| 2011/0177566 | A1 | 7/2011 | Savrasova et al. |

FOREIGN PATENT DOCUMENTS

| | | |
|---|---|---|
| EP | 2138585 | 12/2009 |
| EP | 2246420 | 11/2010 |
| JP | 06-261766 | 9/1994 |
| WO | WO2004/113373 | 12/2004 |

OTHER PUBLICATIONS

Result 3, SEQ ID No. 18747, Kovalic et al. (WO 09/099580 A2), 75.8% seq. identity, search of SEQ ID No. 4 in DNA database of published applications, searched on Jun. 23, 2014.*

Cruz-Ramos, H., et al., "Membrane topology and mutational analysis of *Escherichia coli* CydDC, an ABC-type cysteine exporter required for cytochrome assembly," Microbiol. 2004;150:3415-3427.

Daβler, T., et al., "Identification of a major facilitator protein from *Escherichia coli* involved in efflux of metabolites of the cysteine pathway," Mol. Microbiol. 2000;36(5):1101-1112.

Franke, I., et al., "YfiK from *Escherichia coli* Promotes Export of *O*-Acetylserine and Cysteine," J. Bacteriol. 2003;185(4):1161-1166.

Pittman, M. S., et al., "Cysteine Is Exported from the *Escherichia coli* Cytoplasm by CydDC, an ATP-binding Cassette-type Transporter Required for Cytochrome Assembly," J. Biol. Chem. 2002;277(51):49841-49849.

Yamada, S., et al., "Effect of Drug Transporter Genes on Cysteine Export and Overproduction in *Escherichia coli*," Appl. Environmen. Microbiol. 2006;72(7):4735-4742.

Database UniProt [Online], May 18, 2010, "SubName: Full=Pag0;", retrieved from EBI accession No. UNIPROT: D4GEQ2 on May 19, 2011, Database accession No. D4GEQ2.

Database UniProt [Online], Jul. 28, 2009, "SubName: Full=Permease of the drug/metabolite transporter (DMT) superfamily;", retrieved from EBI accession No. UNIPROT: C4UQA8 on May 19, 2011, Database accession No. C4UQA8.

Database UniProt [Online], May 29, 2007, "SubName: Full=Putative uncharacterized protein;" retrieved from EBI accession No. UNIPROT: A4WAC5 on May 20, 2011, Database accession No. A4WAC5.

De Maayer, P., et al., "Genome Announcements: Genome Sequence of *Pantoea ananatis* LMG20103, the Causative Agent of *Eucalyptus* Blight and Dieback," J. Bacteriol. 2010;192(11):2936-2937.

Partial European Search Report for EP Patent App. No. 11000006.4 (Jun. 8, 2011).

Database UniProt [Online] Database accession No. D4GDT3, retrieved Sep. 8, 2011.

Database UniProt [Online] Database accession No. B2VF51, retrieved Sep. 8, 2011.

Database UniProt [Online] Database accession No. D4GDT4, retrieved Sep. 8, 2011.

Database UniProt [Online] Database accession No. D0KJT0, retrieved Sep. 8, 2011.

Zakataeva, N. P., et al., "Export of Metabolites by the Proteins of the DMT and RhtB Families and Its Possible Role in Intercellular Communication," Microbiol. 2006;75(4):438-448.

European Search Report for EP Patent App. No. 11000006.4 (Aug. 24, 2011).

Third Party Observation filed on Sep. 24, 2012 for the corresponding EP Patent App. No. 11000006.4 and English language translation thereof.

Kössel, H., "Signal-Strukturen der Genexpression," Biologie in unserer Zeit, vol. 12, No. 2, 1982, pp. 39-48, (enclosure to the observation).

Result 2, Geneseq protein database search, Breton et al., US 6,610,836 B1, protein of SEQ ID No. 9714, searched Feb. 25, 2013.

* cited by examiner

SEQUENCE LISTING

```
<160> NUMBER OF SEQ ID NOS: 44

<210> SEQ ID NO 1
<211> LENGTH: 906
<212> TYPE: DNA
<213> ORGANISM: Pantoea ananatis
<220> FEATURE:
<221> NAME/KEY: CDS
<222> LOCATION: (1)..(906)

<400> SEQUENCE: 1

atg aac gca tta ctc tat gct gtg gtc gtg gtt atc tgg ggt aca acc       48
Met Asn Ala Leu Leu Tyr Ala Val Val Val Val Ile Trp Gly Thr Thr
1               5                   10                  15

tgg att gcc atc ttt ttg caa caa ggg ccc gtt gat gtc acg gtg tcc       96
Trp Ile Ala Ile Phe Leu Gln Gln Gly Pro Val Asp Val Thr Val Ser
            20                  25                  30

gtt ttc tgg cgc ttc gcc ata gcc agt att tta ttg ctg acg ctc ctg      144
Val Phe Trp Arg Phe Ala Ile Ala Ser Ile Leu Leu Leu Thr Leu Leu
        35                  40                  45

cag ata atg ggg cgc ctg cgc aga tta tcg ccg cgc gat cat ctg ttt      192
Gln Ile Met Gly Arg Leu Arg Arg Leu Ser Pro Arg Asp His Leu Phe
    50                  55                  60

tgc gct ttg cag ggc tgc tgt gta ttt tgc ttt aat ttt tgg tgc ttt      240
Cys Ala Leu Gln Gly Cys Cys Val Phe Cys Phe Asn Phe Trp Cys Phe
65                  70                  75                  80

tac acc gcc gcc ggt tat atc aat acc ggt tta gag tcc gtg att ttt      288
Tyr Thr Ala Ala Gly Tyr Ile Asn Thr Gly Leu Glu Ser Val Ile Phe
                85                  90                  95

tcc atg gcg gtg ctg tat aac gca gta aac agt tat ctg ttt ttt ggg      336
Ser Met Ala Val Leu Tyr Asn Ala Val Asn Ser Tyr Leu Phe Phe Gly
            100                 105                 110

cag cgc ccc cag ccg cgt ttc tgg ttt gcg gtc acg ctg gga tta acg      384
Gln Arg Pro Gln Pro Arg Phe Trp Phe Ala Val Thr Leu Gly Leu Thr
        115                 120                 125

ggc atg atc ctg ttg ttt tgg gac gat ctg cac atc agc ggc gca agc      432
Gly Met Ile Leu Leu Phe Trp Asp Asp Leu His Ile Ser Gly Ala Ser
    130                 135                 140

ggt gga ctg tgg cga ggc atc ggc ctg tcg gcg ttg ggc acg ttt ggc      480
Gly Gly Leu Trp Arg Gly Ile Gly Leu Ser Ala Leu Gly Thr Phe Gly
145                 150                 155                 160

ttt tct ctg ggc aac atg atc agc ctg cgg cat cag cgc aga cag ctg      528
Phe Ser Leu Gly Asn Met Ile Ser Leu Arg His Gln Arg Arg Gln Leu
                165                 170                 175

gaa acc atg acc act aac gcc tgg gct atg tta tac ggc gca atg gtc      576
Glu Thr Met Thr Thr Asn Ala Trp Ala Met Leu Tyr Gly Ala Met Val
            180                 185                 190
```

```
atg ggc att atc gct cta ctt cgt ggc gtg agt ttc tca ccg ctc tgg      624
Met Gly Ile Ile Ala Leu Leu Arg Gly Val Ser Phe Ser Pro Leu Trp
        195                 200                 205

aca ctg agc tac ctc agt gcc ttg ctt tat ttg tcc ata ttc ggt tcg      672
Thr Leu Ser Tyr Leu Ser Ala Leu Leu Tyr Leu Ser Ile Phe Gly Ser
    210                 215                 220

gtc att gcg ttt tgg gcg tat ttc acc ctg gtc aga cgt acg ggc gcc      720
Val Ile Ala Phe Trp Ala Tyr Phe Thr Leu Val Arg Arg Thr Gly Ala
225                 230                 235                 240

gct aaa gcc gca tac aca aca ctg atg ttt ccg ttg gtt gcc ctc acc      768
Ala Lys Ala Ala Tyr Thr Thr Leu Met Phe Pro Leu Val Ala Leu Thr
                245                 250                 255

tta tcg acg gtt tat gaa ggc tat cac tgg caa agc cac agc gtg gtg      816
Leu Ser Thr Val Tyr Glu Gly Tyr His Trp Gln Ser His Ser Val Val
            260                 265                 270

gga ttg ctg atg atc ctg ggc ggt aac ctg gtg atg ttc gga cgt ccc      864
Gly Leu Leu Met Ile Leu Gly Gly Asn Leu Val Met Phe Gly Arg Pro
        275                 280                 285

ttg cgc tgg cca aaa ccg aaa ccc atg ccg ggc acg cta taa              906
Leu Arg Trp Pro Lys Pro Lys Pro Met Pro Gly Thr Leu
    290                 295                 300


<210> SEQ ID NO 2
<211> LENGTH: 301
<212> TYPE: PRT
<213> ORGANISM: Pantoea ananatis

<400> SEQUENCE: 2

Met Asn Ala Leu Leu Tyr Ala Val Val Val Val Ile Trp Gly Thr Thr
1               5                   10                  15

Trp Ile Ala Ile Phe Leu Gln Gln Gly Pro Val Asp Val Thr Val Ser
            20                  25                  30

Val Phe Trp Arg Phe Ala Ile Ala Ser Ile Leu Leu Leu Thr Leu Leu
        35                  40                  45

Gln Ile Met Gly Arg Leu Arg Arg Leu Ser Pro Arg Asp His Leu Phe
    50                  55                  60

Cys Ala Leu Gln Gly Cys Cys Val Phe Cys Phe Asn Phe Trp Cys Phe
65                  70                  75                  80

Tyr Thr Ala Ala Gly Tyr Ile Asn Thr Gly Leu Glu Ser Val Ile Phe
                85                  90                  95

Ser Met Ala Val Leu Tyr Asn Ala Val Asn Ser Tyr Leu Phe Phe Gly
            100                 105                 110

Gln Arg Pro Gln Pro Arg Phe Trp Phe Ala Val Thr Leu Gly Leu Thr
        115                 120                 125

Gly Met Ile Leu Leu Phe Trp Asp Asp Leu His Ile Ser Gly Ala Ser
    130                 135                 140

Gly Gly Leu Trp Arg Gly Ile Gly Leu Ser Ala Leu Gly Thr Phe Gly
145                 150                 155                 160

Phe Ser Leu Gly Asn Met Ile Ser Leu Arg His Gln Arg Arg Gln Leu
                165                 170                 175

Glu Thr Met Thr Thr Asn Ala Trp Ala Met Leu Tyr Gly Ala Met Val
            180                 185                 190

Met Gly Ile Ile Ala Leu Leu Arg Gly Val Ser Phe Ser Pro Leu Trp
        195                 200                 205

Thr Leu Ser Tyr Leu Ser Ala Leu Leu Tyr Leu Ser Ile Phe Gly Ser
    210                 215                 220

Val Ile Ala Phe Trp Ala Tyr Phe Thr Leu Val Arg Arg Thr Gly Ala
```

```
225                 230                 235                 240

Ala Lys Ala Ala Tyr Thr Thr Leu Met Phe Pro Leu Val Ala Leu Thr
                245                 250                 255

Leu Ser Thr Val Tyr Glu Gly Tyr His Trp Gln Ser His Ser Val Val
            260                 265                 270

Gly Leu Leu Met Ile Leu Gly Gly Asn Leu Val Met Phe Gly Arg Pro
        275                 280                 285

Leu Arg Trp Pro Lys Pro Lys Pro Met Pro Gly Thr Leu
    290                 295                 300


<210> SEQ ID NO 3
<211> LENGTH: 588
<212> TYPE: DNA
<213> ORGANISM: Pantoea ananatis
<220> FEATURE:
<221> NAME/KEY: CDS
<222> LOCATION: (1)..(588)

<400> SEQUENCE: 3

atg ctc gat cct tcc ttc ttt agt tat gtc acc gtg atg tcg att acg       48
Met Leu Asp Pro Ser Phe Phe Ser Tyr Val Thr Val Met Ser Ile Thr
1               5                   10                  15

ccg ggg cca aat aat ctg ttg ctc gcc act tcc ggt gtt aac ttt ggt       96
Pro Gly Pro Asn Asn Leu Leu Leu Ala Thr Ser Gly Val Asn Phe Gly
            20                  25                  30

atg cgc cgg acg tta ccg atg gtg ttt ggc att ttg att ggc tgt gcg      144
Met Arg Arg Thr Leu Pro Met Val Phe Gly Ile Leu Ile Gly Cys Ala
        35                  40                  45

cta caa acc gcc att gcg ggg ctg gcg ctg gaa gtc ctg ctg cac tgg      192
Leu Gln Thr Ala Ile Ala Gly Leu Ala Leu Glu Val Leu Leu His Trp
    50                  55                  60

atg gca tct gtg cgt ctg ccg ctg acg ctg gtg gga tgt ggt tat ttg      240
Met Ala Ser Val Arg Leu Pro Leu Thr Leu Val Gly Cys Gly Tyr Leu
65                  70                  75                  80

tta tgg ctg tca tgg aaa ata ttt cgg gcg aat gcc ccc gaa gcg cgc      288
Leu Trp Leu Ser Trp Lys Ile Phe Arg Ala Asn Ala Pro Glu Ala Arg
                85                  90                  95

gca aag ccg cag ccc atg acc ctg gtg ggt ggg gcc tgt ttt cag gct      336
Ala Lys Pro Gln Pro Met Thr Leu Val Gly Gly Ala Cys Phe Gln Ala
            100                 105                 110

atc aat cca aaa gcc tgg tta atg gcc agc aac gtg gca ctg ctc tac      384
Ile Asn Pro Lys Ala Trp Leu Met Ala Ser Asn Val Ala Leu Leu Tyr
        115                 120                 125

agc gcc agc agt ggc gtg ctg acc gtg atg ggg gct ttt atg ttg ctc      432
Ser Ala Ser Ser Gly Val Leu Thr Val Met Gly Ala Phe Met Leu Leu
    130                 135                 140

aat ctg ccg tgc att tta ttg tgg gct gca ctg ggt gac cgc ctg cgc      480
Asn Leu Pro Cys Ile Leu Leu Trp Ala Ala Leu Gly Asp Arg Leu Arg
145                 150                 155                 160

ggt cac ctg caa atc aac tgg aaa cgc cag ctg ttt aac agc ctg atg      528
Gly His Leu Gln Ile Asn Trp Lys Arg Gln Leu Phe Asn Ser Leu Met
                165                 170                 175

gcg ctg tcg ctg gtg gcg acc acg atc tgg atg ctg gtc gat gcc ttc      576
Ala Leu Ser Leu Val Ala Thr Thr Ile Trp Met Leu Val Asp Ala Phe
            180                 185                 190

agg ctt ctc tag                                                      588
Arg Leu Leu
        195


<210> SEQ ID NO 4
```

<211> LENGTH: 195
<212> TYPE: PRT
<213> ORGANISM: Pantoea ananatis

<400> SEQUENCE: 4

```
Met Leu Asp Pro Ser Phe Phe Ser Tyr Val Thr Val Met Ser Ile Thr
1               5                   10                  15

Pro Gly Pro Asn Asn Leu Leu Leu Ala Thr Ser Gly Val Asn Phe Gly
            20                  25                  30

Met Arg Arg Thr Leu Pro Met Val Phe Gly Ile Leu Ile Gly Cys Ala
        35                  40                  45

Leu Gln Thr Ala Ile Ala Gly Leu Ala Leu Glu Val Leu Leu His Trp
    50                  55                  60

Met Ala Ser Val Arg Leu Pro Leu Thr Leu Val Gly Cys Gly Tyr Leu
65                  70                  75                  80

Leu Trp Leu Ser Trp Lys Ile Phe Arg Ala Asn Ala Pro Glu Ala Arg
                85                  90                  95

Ala Lys Pro Gln Pro Met Thr Leu Val Gly Gly Ala Cys Phe Gln Ala
            100                 105                 110

Ile Asn Pro Lys Ala Trp Leu Met Ala Ser Asn Val Ala Leu Leu Tyr
        115                 120                 125

Ser Ala Ser Ser Gly Val Leu Thr Val Met Gly Ala Phe Met Leu Leu
    130                 135                 140

Asn Leu Pro Cys Ile Leu Leu Trp Ala Ala Leu Gly Asp Arg Leu Arg
145                 150                 155                 160

Gly His Leu Gln Ile Asn Trp Lys Arg Gln Leu Phe Asn Ser Leu Met
                165                 170                 175

Ala Leu Ser Leu Val Ala Thr Thr Ile Trp Met Leu Val Asp Ala Phe
            180                 185                 190

Arg Leu Leu
        195
```

<210> SEQ ID NO 5
<211> LENGTH: 1491
<212> TYPE: DNA
<213> ORGANISM: Pantoea ananatis
<220> FEATURE:
<221> NAME/KEY: CDS
<222> LOCATION: (1)..(1491)

<400> SEQUENCE: 5

```
gtg tcc cct gaa acc cag tcc gag cac aga ctt tat cag caa ctg gcc       48
Val Ser Pro Glu Thr Gln Ser Glu His Arg Leu Tyr Gln Gln Leu Ala
1               5                   10                  15

gac agc ttt gcc gag gcc att cac aag ggc acg cta aaa ccg ggc aag       96
Asp Ser Phe Ala Glu Ala Ile His Lys Gly Thr Leu Lys Pro Gly Lys
            20                  25                  30

cgc ttg ccc gcc atc cgg cgc gtt gct cag tca cat caa gtc agc gtg      144
Arg Leu Pro Ala Ile Arg Arg Val Ala Gln Ser His Gln Val Ser Val
        35                  40                  45

aac acc gtg ctg aat gcc tgg cag ctg ctg gag aat cgc ggt ctg att      192
Asn Thr Val Leu Asn Ala Trp Gln Leu Leu Glu Asn Arg Gly Leu Ile
    50                  55                  60

gag gcg cgc ccg caa tcg ggc tac tac gtg cgc ggc gtg ctg ccg gtg      240
Glu Ala Arg Pro Gln Ser Gly Tyr Tyr Val Arg Gly Val Leu Pro Val
65                  70                  75                  80

gtg acg cga gat gcc cag cac tct tcc cgg gtg gtt cgc gat cca ggc      288
Val Thr Arg Asp Ala Gln His Ser Ser Arg Val Val Arg Asp Pro Gly
                85                  90                  95
```

-continued

```
aac gag aag ctg gac ttg att gat aag gtt ttc gcc gca caa aat cat      336
Asn Glu Lys Leu Asp Leu Ile Asp Lys Val Phe Ala Ala Gln Asn His
            100                 105                 110

ccg gat tac acc aat att tcg ctg gcc tgt ccg cag gac agt gac ctg      384
Pro Asp Tyr Thr Asn Ile Ser Leu Ala Cys Pro Gln Asp Ser Asp Leu
        115                 120                 125

ttt ccg tca gcc aga ctg gcg cgc att acg gcc tct ctg cta cgt cgc      432
Phe Pro Ser Ala Arg Leu Ala Arg Ile Thr Ala Ser Leu Leu Arg Arg
    130                 135                 140

gat cca caa ctt att ggt cgc tac gcg ctt ccg ccg ggt agt gag cgc      480
Asp Pro Gln Leu Ile Gly Arg Tyr Ala Leu Pro Pro Gly Ser Glu Arg
145                 150                 155                 160

tta cgg gag gag att gcg cga cgt gcc ttg cat agt ggc cag tcg ctc      528
Leu Arg Glu Glu Ile Ala Arg Arg Ala Leu His Ser Gly Gln Ser Leu
                165                 170                 175

gcc gcc gat gag atc acc ctt acc cat ggc tgc atg gag gca ctt cag      576
Ala Ala Asp Glu Ile Thr Leu Thr His Gly Cys Met Glu Ala Leu Gln
            180                 185                 190

ctg gca ctc agg gcg gtg acc cgg ccg ggt gat tgt gtc ggt ctg gaa      624
Leu Ala Leu Arg Ala Val Thr Arg Pro Gly Asp Cys Val Gly Leu Glu
        195                 200                 205

tcc ccc acc tat ttc ttc ctg ttt ccc ctg ctg gca tcg ctg ggc ctg      672
Ser Pro Thr Tyr Phe Phe Leu Phe Pro Leu Leu Ala Ser Leu Gly Leu
    210                 215                 220

aag gca ctg gag att cct acc gat cct cag cgc ggc ctg tcg ctg gat      720
Lys Ala Leu Glu Ile Pro Thr Asp Pro Gln Arg Gly Leu Ser Leu Asp
225                 230                 235                 240

gca ctt gag atg ctg ctc cag gaa aag cgt att cag gcg ctg gtt gcc      768
Ala Leu Glu Met Leu Leu Gln Glu Lys Arg Ile Gln Ala Leu Val Ala
                245                 250                 255

atg ccc tct gcg cag aac ccg ctg ggc ttt gga atg tcg ttg ccc gac      816
Met Pro Ser Ala Gln Asn Pro Leu Gly Phe Gly Met Ser Leu Pro Asp
            260                 265                 270

aag aaa agg ctc gca aag tta gta aac act tac aac gtt cct ttg att      864
Lys Lys Arg Leu Ala Lys Leu Val Asn Thr Tyr Asn Val Pro Leu Ile
        275                 280                 285

gag gac ggg ctt tac gat gag ttg cag ttt gac tgg ccg ctg tct cct      912
Glu Asp Gly Leu Tyr Asp Glu Leu Gln Phe Asp Trp Pro Leu Ser Pro
    290                 295                 300

acg gtg aag tca ttc gat cag cat ggc tgg gtg ctc tac tgc acc agt      960
Thr Val Lys Ser Phe Asp Gln His Gly Trp Val Leu Tyr Cys Thr Ser
305                 310                 315                 320

ttc acg aaa acc gtt gcg ccc gat ttt cgc atc ggc tgg att gca gcc     1008
Phe Thr Lys Thr Val Ala Pro Asp Phe Arg Ile Gly Trp Ile Ala Ala
                325                 330                 335

ggc cgc ttt cat gat gcc att gca cgc ctt aaa gcc gtg tca tcc atg     1056
Gly Arg Phe His Asp Ala Ile Ala Arg Leu Lys Ala Val Ser Ser Met
            340                 345                 350

gcg gaa tcg gcc ctg ctg tct gaa acc ctg gca gaa ttt ctt gcc aac     1104
Ala Glu Ser Ala Leu Leu Ser Glu Thr Leu Ala Glu Phe Leu Ala Asn
        355                 360                 365

gga ggt tac gac cac cat ctg cgc agc ctg cgc cgt agc tat gcc agc     1152
Gly Gly Tyr Asp His His Leu Arg Ser Leu Arg Arg Ser Tyr Ala Ser
    370                 375                 380

aat ctg gat gaa gcg cgc ggt ttg att gcg cag cat ttt cct cag ggt     1200
Asn Leu Asp Glu Ala Arg Gly Leu Ile Ala Gln His Phe Pro Gln Gly
385                 390                 395                 400

acc cgg gct acg tta ccg cgc ggc ggc ttc gtt ttt tgg gtc gaa ctg     1248
Thr Arg Ala Thr Leu Pro Arg Gly Gly Phe Val Phe Trp Val Glu Leu
```

-continued

```
                405                 410                 415

ccc ggc aat gtg aat acc aca gag atg ttt acc cgt ctg ttg aaa gag     1296
Pro Gly Asn Val Asn Thr Thr Glu Met Phe Thr Arg Leu Leu Lys Glu
            420                 425                 430

cag att tgt gtc acg cca ggt gca ctg tat tcg ctg agc gag cgc tat     1344
Gln Ile Cys Val Thr Pro Gly Ala Leu Tyr Ser Leu Ser Glu Arg Tyr
        435                 440                 445

aac cat gca ttg cgc ctc tca tgc tgc tat ccg ttt gat cag cgc tat     1392
Asn His Ala Leu Arg Leu Ser Cys Cys Tyr Pro Phe Asp Gln Arg Tyr
    450                 455                 460

gtt cgc gcc atc atc cgc gcg ggg gcg gtt gcc tgc gaa ctc gct ggc     1440
Val Arg Ala Ile Ile Arg Ala Gly Ala Val Ala Cys Glu Leu Ala Gly
465                 470                 475                 480

ctg cca ccg ggc cgg gat cag ggc gtg cca tta cgt ccc caa atg gta     1488
Leu Pro Pro Gly Arg Asp Gln Gly Val Pro Leu Arg Pro Gln Met Val
                485                 490                 495

tag                                                                 1491


<210> SEQ ID NO 6
<211> LENGTH: 496
<212> TYPE: PRT
<213> ORGANISM: Pantoea ananatis

<400> SEQUENCE: 6

Val Ser Pro Glu Thr Gln Ser Glu His Arg Leu Tyr Gln Gln Leu Ala
1               5                   10                  15

Asp Ser Phe Ala Glu Ala Ile His Lys Gly Thr Leu Lys Pro Gly Lys
            20                  25                  30

Arg Leu Pro Ala Ile Arg Arg Val Ala Gln Ser His Gln Val Ser Val
        35                  40                  45

Asn Thr Val Leu Asn Ala Trp Gln Leu Leu Glu Asn Arg Gly Leu Ile
    50                  55                  60

Glu Ala Arg Pro Gln Ser Gly Tyr Tyr Val Arg Gly Val Leu Pro Val
65                  70                  75                  80

Val Thr Arg Asp Ala Gln His Ser Ser Arg Val Val Arg Asp Pro Gly
                85                  90                  95

Asn Glu Lys Leu Asp Leu Ile Asp Lys Val Phe Ala Ala Gln Asn His
            100                 105                 110

Pro Asp Tyr Thr Asn Ile Ser Leu Ala Cys Pro Gln Asp Ser Asp Leu
        115                 120                 125

Phe Pro Ser Ala Arg Leu Ala Arg Ile Thr Ala Ser Leu Leu Arg Arg
    130                 135                 140

Asp Pro Gln Leu Ile Gly Arg Tyr Ala Leu Pro Pro Gly Ser Glu Arg
145                 150                 155                 160

Leu Arg Glu Glu Ile Ala Arg Arg Ala Leu His Ser Gly Gln Ser Leu
                165                 170                 175

Ala Ala Asp Glu Ile Thr Leu Thr His Gly Cys Met Glu Ala Leu Gln
            180                 185                 190

Leu Ala Leu Arg Ala Val Thr Arg Pro Gly Asp Cys Val Gly Leu Glu
        195                 200                 205

Ser Pro Thr Tyr Phe Phe Leu Phe Pro Leu Leu Ala Ser Leu Gly Leu
    210                 215                 220

Lys Ala Leu Glu Ile Pro Thr Asp Pro Gln Arg Gly Leu Ser Leu Asp
225                 230                 235                 240

Ala Leu Glu Met Leu Leu Gln Glu Lys Arg Ile Gln Ala Leu Val Ala
                245                 250                 255
```

```
Met Pro Ser Ala Gln Asn Pro Leu Gly Phe Gly Met Ser Leu Pro Asp
            260                 265                 270

Lys Lys Arg Leu Ala Lys Leu Val Asn Thr Tyr Asn Val Pro Leu Ile
        275                 280                 285

Glu Asp Gly Leu Tyr Asp Glu Leu Gln Phe Asp Trp Pro Leu Ser Pro
    290                 295                 300

Thr Val Lys Ser Phe Asp Gln His Gly Trp Val Leu Tyr Cys Thr Ser
305                 310                 315                 320

Phe Thr Lys Thr Val Ala Pro Asp Phe Arg Ile Gly Trp Ile Ala Ala
                325                 330                 335

Gly Arg Phe His Asp Ala Ile Ala Arg Leu Lys Ala Val Ser Ser Met
            340                 345                 350

Ala Glu Ser Ala Leu Leu Ser Glu Thr Leu Ala Glu Phe Leu Ala Asn
        355                 360                 365

Gly Gly Tyr Asp His His Leu Arg Ser Leu Arg Arg Ser Tyr Ala Ser
    370                 375                 380

Asn Leu Asp Glu Ala Arg Gly Leu Ile Ala Gln His Phe Pro Gln Gly
385                 390                 395                 400

Thr Arg Ala Thr Leu Pro Arg Gly Gly Phe Val Phe Trp Val Glu Leu
                405                 410                 415

Pro Gly Asn Val Asn Thr Thr Glu Met Phe Thr Arg Leu Leu Lys Glu
            420                 425                 430

Gln Ile Cys Val Thr Pro Gly Ala Leu Tyr Ser Leu Ser Glu Arg Tyr
        435                 440                 445

Asn His Ala Leu Arg Leu Ser Cys Cys Tyr Pro Phe Asp Gln Arg Tyr
    450                 455                 460

Val Arg Ala Ile Ile Arg Ala Gly Ala Val Ala Cys Glu Leu Ala Gly
465                 470                 475                 480

Leu Pro Pro Gly Arg Asp Gln Gly Val Pro Leu Arg Pro Gln Met Val
                485                 490                 495
```

<210> SEQ ID NO 7
<211> LENGTH: 28
<212> TYPE: DNA
<213> ORGANISM: Artificial sequence
<220> FEATURE:
<223> OTHER INFORMATION: primer P1

<400> SEQUENCE: 7
cgcggatcct gtttacggta atcctgtc 28

<210> SEQ ID NO 8
<211> LENGTH: 26
<212> TYPE: DNA
<213> ORGANISM: Artificial sequence
<220> FEATURE:
<223> OTHER INFORMATION: primer P2

<400> SEQUENCE: 8
cgcggatcca caagtgcagg gctttc 26

<210> SEQ ID NO 9
<211> LENGTH: 27
<212> TYPE: DNA
<213> ORGANISM: Artificial sequence
<220> FEATURE:
<223> OTHER INFORMATION: primer P3

<400> SEQUENCE: 9
cgcggatcca gccgtatcct gcagctc 27

<210> SEQ ID NO 10
<211> LENGTH: 27
<212> TYPE: DNA
<213> ORGANISM: Artificial sequence
<220> FEATURE:
<223> OTHER INFORMATION: primer P4

<400> SEQUENCE: 10
cgcggatcct gtaaaggctg gtcccac 27

<210> SEQ ID NO 11
<211> LENGTH: 313
<212> TYPE: DNA
<213> ORGANISM: Artificial sequence
<220> FEATURE:
<223> OTHER INFORMATION: Promoter Pnlp0

<400> SEQUENCE: 11
gcatgcttcc aactgcgcta atgacgcagc tggacgaagg cgggattctc gtcttacccg 60
taggggagga gcaccagtat ttgaaacggg tgcgtcgtcg gggaggcgaa tttattatcg 120
ataccgtgga ggccgtgcgc tttgtccctt tagtgaaggg tgagctggct taaaacgtga 180
ggaaatacct ggatttttcc tggttatttt gccgcaggtc agcgtatcgt gaacatcttt 240
tccagtgttc agtagggtgc cttgcacggt aattatgtca ctggttatta accaattttt 300
cctgggggtc gac 313

<210> SEQ ID NO 12
<211> LENGTH: 313
<212> TYPE: DNA
<213> ORGANISM: Artificial sequence
<220> FEATURE:
<223> OTHER INFORMATION: Promoter Pnlp23

<400> SEQUENCE: 12
gcatgcttcc aactgcgcta atgacgcagc tggacgaagg cgggattctc gtcttacccg 60
taggggagga gcaccagtat ttgaaacggg tgcgtcgtcg gggaggcgaa tttattatcg 120
ataccgtgga ggccgtgcgc tttgtccctt tagtgaaggg tgagctggct taaaacgtga 180
ggaaatacct ggatttttcc tggttatttt gccgcaggtc agcgtataat gaagatcttt 240
tccagtgttc agtagggtgc cttgcacggt tataatgtca ctggttatta accaattttt 300
cctgggggtc gac 313

<210> SEQ ID NO 13
<211> LENGTH: 312
<212> TYPE: DNA
<213> ORGANISM: Artificial sequence
<220> FEATURE:
<223> OTHER INFORMATION: Promoter Pnlp8

<400> SEQUENCE: 13
gcatgcttcc aactgcgcta atgacgcagc tggacgaagg cgggattctc gtcttacccg 60
taggggagga gcaccagtat ttgaaacggg tgcgtcgtcg gggaggcgaa tttattatcg 120
ataccgtgga ggccgtgcgc tttgtccctt tagtgaaggg tgagctggct taaaacgtga 180
ggaaatacct ggatttttcc tggttatttt gccgcaggtc agcgtataat gaagatcttt 240
tccagtgttg acaagggtcc ttgcacggtt ataatgtcac tggttattaa ccaatttttc 300

-continued ctgggggtcg ac 312

<210> SEQ ID NO 14
<211> LENGTH: 28
<212> TYPE: DNA
<213> ORGANISM: Artificial sequence
<220> FEATURE:
<223> OTHER INFORMATION: primer P5

<400> SEQUENCE: 14
ccgtcgacat gaacgcatta ctctatgc 28

<210> SEQ ID NO 15
<211> LENGTH: 29
<212> TYPE: DNA
<213> ORGANISM: Artificial sequence
<220> FEATURE:
<223> OTHER INFORMATION: primer P6

<400> SEQUENCE: 15
aatctagatt atagcgtgcc cggcatggg 29

<210> SEQ ID NO 16
<211> LENGTH: 29
<212> TYPE: DNA
<213> ORGANISM: Artificial sequence
<220> FEATURE:
<223> OTHER INFORMATION: primer P7

<400> SEQUENCE: 16
cgcggatcca ggcattcagc acggtgttc 29

<210> SEQ ID NO 17
<211> LENGTH: 28
<212> TYPE: DNA
<213> ORGANISM: Artificial sequence
<220> FEATURE:
<223> OTHER INFORMATION: primer P8

<400> SEQUENCE: 17
acgcgtcgac atgctcgatc cttccttc 28

<210> SEQ ID NO 18
<211> LENGTH: 29
<212> TYPE: DNA
<213> ORGANISM: Artificial sequence
<220> FEATURE:
<223> OTHER INFORMATION: primer P9

<400> SEQUENCE: 18
gctctagact agagaagcct gaaggcatc 29

<210> SEQ ID NO 19
<211> LENGTH: 33
<212> TYPE: DNA
<213> ORGANISM: Artificial sequence
<220> FEATURE:
<223> OTHER INFORMATION: primer P10

<400> SEQUENCE: 19
agctgagtcg acatgtcgtg tgaagaactg gaa 33

<210> SEQ ID NO 20
<211> LENGTH: 33
<212> TYPE: DNA
<213> ORGANISM: Artificial sequence
<220> FEATURE:
<223> OTHER INFORMATION: primer P11

<400> SEQUENCE: 20
agctgatcta gaatagatga ttacatcgca tcc 33

<210> SEQ ID NO 21
<211> LENGTH: 34
<212> TYPE: DNA
<213> ORGANISM: Artificial sequence
<220> FEATURE:
<223> OTHER INFORMATION: primer P12

<400> SEQUENCE: 21
agctgagtcg acaaccctct gttatatgcc ttta 34

<210> SEQ ID NO 22
<211> LENGTH: 33
<212> TYPE: DNA
<213> ORGANISM: Artificial sequence
<220> FEATURE:
<223> OTHER INFORMATION: primer P13

<400> SEQUENCE: 22
agctgagcat gcgagtgaag gttttgtttt gac 33

<210> SEQ ID NO 23
<211> LENGTH: 36
<212> TYPE: DNA
<213> ORGANISM: Artificial sequence
<220> FEATURE:
<223> OTHER INFORMATION: primer P14

<400> SEQUENCE: 23
agctgagtcg acccccagga aaaattggtt aataac 36

<210> SEQ ID NO 24
<211> LENGTH: 33
<212> TYPE: DNA
<213> ORGANISM: Artificial sequence
<220> FEATURE:
<223> OTHER INFORMATION: primer P15

<400> SEQUENCE: 24
agctgagcat gcttccaact gcgctaatga cgc 33

<210> SEQ ID NO 25
<211> LENGTH: 33
<212> TYPE: DNA
<213> ORGANISM: Artificial sequence
<220> FEATURE:
<223> OTHER INFORMATION: primer P16

<400> SEQUENCE: 25
agctgatcta gaaaacagaa tttgcctggc ggc 33

<210> SEQ ID NO 26
<211> LENGTH: 33
<212> TYPE: DNA
<213> ORGANISM: Artificial sequence
<220> FEATURE:
<223> OTHER INFORMATION: primer P17

<400> SEQUENCE: 26
agctgaggat ccaggaagag tttgtagaaa cgc 33

-continued

<210> SEQ ID NO 27
<211> LENGTH: 32
<212> TYPE: DNA
<213> ORGANISM: Artificial sequence
<220> FEATURE:
<223> OTHER INFORMATION: primer P18

<400> SEQUENCE: 27
agctgagtcg acgtgttcgc tgaatacggg gt 32

<210> SEQ ID NO 28
<211> LENGTH: 32
<212> TYPE: DNA
<213> ORGANISM: Artificial sequence
<220> FEATURE:
<223> OTHER INFORMATION: primer P19

<400> SEQUENCE: 28
agctgatcta gagaaagcat caggattgca gc 32

<210> SEQ ID NO 29
<211> LENGTH: 59
<212> TYPE: DNA
<213> ORGANISM: Artificial sequence
<220> FEATURE:
<223> OTHER INFORMATION: primer P20
<220> FEATURE:
<221> NAME/KEY: misc_feature
<222> LOCATION: (1)..(59)
<223> OTHER INFORMATION: “n”- any nucleotide

<400> SEQUENCE: 29
atcgtgaaga tcttttccag tgttnannag ggtgccttgc acggtnatna ngtcactgg 59

<210> SEQ ID NO 30
<211> LENGTH: 32
<212> TYPE: DNA
<213> ORGANISM: Artificial sequence
<220> FEATURE:
<223> OTHER INFORMATION: primer P21
<220> FEATURE:
<221> NAME/KEY: misc_feature
<222> LOCATION: (16)..(20)
<223> OTHER INFORMATION: “n”-any nucleotide

<400> SEQUENCE: 30
tggaaaagat cttctnnnnn cgctgacctg cg 32

<210> SEQ ID NO 31
<211> LENGTH: 60
<212> TYPE: DNA
<213> ORGANISM: Artificial sequence
<220> FEATURE:
<223> OTHER INFORMATION: primer P22

<400> SEQUENCE: 31
tccgctcacg attttttca tcgctggtaa ggtcatttat cccccaggaa aaattggtta 60

<210> SEQ ID NO 32
<211> LENGTH: 64
<212> TYPE: DNA
<213> ORGANISM: Artificial sequence
<220> FEATURE:
<223> OTHER INFORMATION: primer P23

<400> SEQUENCE: 32
tttcacaccg ctcaaccgca gggcataacc ggcccttgaa gcctgctttt ttatactaag 60
ttgg 64

<210> SEQ ID NO 33
<211> LENGTH: 20
<212> TYPE: DNA
<213> ORGANISM: Artificial sequence
<220> FEATURE:
<223> OTHER INFORMATION: primer P24

<400> SEQUENCE: 33
ctttgtccct ttagtgaagg 20

<210> SEQ ID NO 34
<211> LENGTH: 44
<212> TYPE: DNA
<213> ORGANISM: Artificial sequence
<220> FEATURE:
<223> OTHER INFORMATION: primer P25

<400> SEQUENCE: 34
agctgatcta gaagctgact cgagttaatg gcctcccaga cgac 44

<210> SEQ ID NO 35
<211> LENGTH: 33
<212> TYPE: DNA
<213> ORGANISM: Artificial sequence
<220> FEATURE:
<223> OTHER INFORMATION: primer P26

<400> SEQUENCE: 35
agctgagtcg acatggcaaa ggtatcactg gaa 33

<210> SEQ ID NO 36
<211> LENGTH: 34
<212> TYPE: DNA
<213> ORGANISM: Artificial sequence
<220> FEATURE:
<223> OTHER INFORMATION: primer P27

<400> SEQUENCE: 36
gagaacgccc gggcgggctt cgtgaatatg cagc 34

<210> SEQ ID NO 37
<211> LENGTH: 32
<212> TYPE: DNA
<213> ORGANISM: Artificial sequence
<220> FEATURE:
<223> OTHER INFORMATION: primer P28

<400> SEQUENCE: 37
agctgatcta gacgtgggat cagtaaagca gg 32

<210> SEQ ID NO 38
<211> LENGTH: 22
<212> TYPE: DNA
<213> ORGANISM: Artificial sequence
<220> FEATURE:
<223> OTHER INFORMATION: primer P29

<400> SEQUENCE: 38
aaaaccgccc gggcgttctc ac 22

<210> SEQ ID NO 39
<211> LENGTH: 39
<212> TYPE: DNA

-continued

```
<213> ORGANISM: Artificial sequence
<220> FEATURE:
<223> OTHER INFORMATION: primer P30

<400> SEQUENCE: 39

agctgagtcg accccgtggt ggcaaccttt aaaaaactg                             39


<210> SEQ ID NO 40
<211> LENGTH: 43
<212> TYPE: DNA
<213> ORGANISM: Artificial sequence
<220> FEATURE:
<223> OTHER INFORMATION: primer P31

<400> SEQUENCE: 40

agctgaaagc ttgcatgcac gcgtggcgat ctggcctgac tgc                        43


<210> SEQ ID NO 41
<211> LENGTH: 33
<212> TYPE: DNA
<213> ORGANISM: Artificial sequence
<220> FEATURE:
<223> OTHER INFORMATION: primer P32

<400> SEQUENCE: 41

agctgatcta gaaaacagaa tttgcctggc ggc                                   33


<210> SEQ ID NO 42
<211> LENGTH: 33
<212> TYPE: DNA
<213> ORGANISM: Artificial sequence
<220> FEATURE:
<223> OTHER INFORMATION: primer P33

<400> SEQUENCE: 42

agctgaggat ccaggaagag tttgtagaaa cgc                                   33


<210> SEQ ID NO 43
<211> LENGTH: 33
<212> TYPE: DNA
<213> ORGANISM: Artificial sequence
<220> FEATURE:
<223> OTHER INFORMATION: primer P34

<400> SEQUENCE: 43

agctgatcta gaagtctccg atgctattaa tcc                                   33


<210> SEQ ID NO 44
<211> LENGTH: 35
<212> TYPE: DNA
<213> ORGANISM: Artificial sequence
<220> FEATURE:
<223> OTHER INFORMATION: primer P35

<400> SEQUENCE: 44

agctgagtcg acgtgagtac attagaacaa acaat                                 35
```

METHOD FOR PRODUCING AN L-AMINO ACID USING A BACTERIUM OF THE ENTEROBACTERIACEAE FAMILY

This application is a Divisional of, and claims priority under 35 U.S.C. §120 to, U.S. patent application Ser. No. 13/004,188, filed Jan. 11, 2011, and claims priority there-through under 35 U.S.C. §119 to Russian Patent Application No. 2010101136, filed on Jan. 15, 2010, the entireties of which are incorporated by reference herein. The Sequence Listing in electronic format filed herewith is also hereby incorporated by reference in its entirety (File Name: 2013-05-03T_US-454D_Seq_List; File Size: 31 KB; Date Created: May 3, 2013).

BACKGROUND OF THE INVENTION

1. Technical Field

The present invention relates to the microbiological industry, and specifically to a method for producing an L-amino acid using a bacterium of the Enterobacteriaceae family which has a protein derived from a bacterium belonging to the genus *Pantoea*, and the protein is able to confer resistance to cysteine.

2. Description of the Related Art

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acid production yields have been reported, including transformation of microorganisms with recombinant DNA (U.S. Pat. No. 4,278,765). Other techniques for enhancing production yields include increasing the activities of enzymes involved in amino acid biosynthesis and/or desensitizing the target enzymes to feedback inhibition by the resulting L-amino acid (U.S. Pat. Nos. 4,346,170; 5,661,012; and 6,040,160).

A new microbial strain is disclosed which is suitable for the fermentative production of L-cysteine, L-cystine, N-acetylserine which is produced from the non-enzymatic conversion of O-acetyl-L-serine, and/or thiazolidine derivatives. This new strain overexpresses at least one gene which codes for a protein that mediates cellular clearance of antibiotics or other substances that are toxic for the microorganism (EP 0885962).

A chromosomal fragment has been identified in a gene bank from *Escherichia coli*, which is able to increase the yield of cysteine in an industrial production strain. Subcloning and genetic analysis showed that an open reading frame coding for a product of 299 amino acids, called Orf299, was responsible. The Orf299 was synthesized in the T7 polymerase/promoter system and exhibited the properties of an integral membrane protein. These results further indicated that ORF299 codes for an export pump responsible for excreting different metabolites of the cysteine pathway (Dassler T. et al, Mol. Microbiol.; 36(5): 1101-12 (2000).

The ORF yfiK gene was discovered to be able to increase cysteine production when overexpressed in an industrial *E. coli* production strain. The yfiK gene product is an integral membrane protein with about six predicted transmembrane helices, and it belongs to the RhtB family of export proteins. YfiK overproduction from a plasmid leads to drastic and parallel secretion of O-acetyl-L-serine and cysteine into the medium, but only when the organism possesses a serine transacetylase that is insensitive to feedback inhibition by cysteine. When excess O-acetyl-L-serine is added to the medium, this requirement for the presence of a feedback-insensitive serine transacetylase during cysteine secretion can be obviated both in the yfiK-carrying transformant and in the wild-type strain. A delta yfiK mutant did not show any phenotype, and was able to export O-acetyl-L-serine and cysteine when transformed with a plasmid carrying ydeD, a previously characterized, alternate O-acetyl-L-serine/cysteine exporter. Since an ydeD-yfiK double mutant showed the same pattern, it appears that YfiK and YdeD act independently. The necessity for the cell to regulate the size of the internal pool of O-acetyl-L-serine via synthesis of exporter proteins could be connected to the fact that this compound (when supplied externally) inhibits growth. Overexpression of either ydeD or yfiK alleviates this inhibition, and increases resistance to azaserine, which is an analog of O-acetyl-L-serine (Franke I et. al., J. Bacteriol.; 185(4):1161-6 (2003)).

Assembly of *E. coli* cytochrome bd and periplasmic cytochromes requires the ATP-binding cassette transporter CydDC, the substrate of which is unknown. Two-dimensional SDS-PAGE comparison of periplasm from wild-type and cydD mutant strains revealed that the latter was deficient in several periplasmic transport binding proteins, even though no single major protein was missing in the cydD periplasm. Instead, CydDC exports from the cytoplasm to the periplasm the amino acid cysteine, which can be further demonstrated by using reverted membrane vesicles that transport radiolabeled cysteine inward in an ATP-dependent, uncoupled-independent manner. New pleiotropic cydD phenotypes have been reported, including ones with sensitivity to benzylpenicillin and dithiothreitol, and ones with loss of motility. Both of these phenotypes are consistent with periplasmic defects in disulfide bond formation. The presence of exogenous cysteine was able to reverse these phenotypes and affect the levels of periplasmic c-type cytochromes in cydD and wild-type strains, but did not restore cytochrome d. Consistent with CydDC being a cysteine exporter, cydD mutant growth was hypersensitive to high cysteine concentrations and produced higher cytoplasmic cysteine levels, as did a mutant defective in ORF299 which encoded a transporter of the major facilitator superfamily. A cydD ORF299 double mutant was extremely cysteine-sensitive and had higher cytoplasmic cysteine levels, whereas CydDC overexpression conferred resistance to high extracellular cysteine concentrations. It seems likely that CydDC is responsible for the export of cysteine, which is crucial for redox homeostasis in the periplasm (Pittman M. S. et al., J Biol. Chem.; 277(51):49841-9 (2002)).

In addition to YdeD and YfiK, which have been previously reported as L-cysteine exporter proteins in *E. coli*, the effects of 33 putative drug transporter genes in *E. coli* on L-cysteine export and overproduction was analyzed. Overexpression of the acrD, acrEF, bcr, cusA, emrAB, emrKY, ybjYZ, and yojlH genes reversed the growth inhibition of tnaA-disrupted *E. coli* cells by L-cysteine. The tnaA gene is the major cysteine desulfhydrase gene. It was found that overexpression of these eight genes reduces intracellular L-cysteine levels after cultivation in the presence of L-cysteine. Amino acid transport assays showed that Bcr overexpression, which confers bicyclomycin and tetracycline resistance, specifically promotes L-cysteine export driven by the energy generated from the proton gradient. When a tnaA-disrupted *E. coli* strain expressing the altered cysE gene was transformed with a plasmid carrying the bcr gene, the transformant produced more L-cysteine than cells carrying the vector only. A reporter gene assay suggested that the bcr gene is constitutively expressed at substantial levels. These results indicate that the multidrug transporter Bcr in the major facilitator family is involved in L-cysteine export and overproduction in genetically engineered *E. coli* cells (Yamada S. et al., Appl Environ Microbiol.; 72(7):4735-42 (2006)).

But currently, there have been no reports of using a bacterium having a protein derived from bacteria belonging to the genus *Pantoea*, and which is able to confer resistance to growth inhibition by L-cysteine in the bacterium, for the purpose of producing L-amino acids.

SUMMARY OF THE INVENTION

Aspects of the presently disclosed subject matter can include enhancing the productivity of L-amino acid-producing strains and providing a method for producing non-aromatic or aromatic L-amino acids using these strains.

The above aspects were achieved by finding that a protein activity which confers to a bacterium resistance to growth inhibition by L-cysteine can result in enhancing production of L-amino acids, such as L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-phenylalanine, L-tyrosine, and L-tryptophan.

Another aspect of the present invention includes a bacterium of the Enterobacteriaceae family having an increased ability to produce amino acids, such as L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-phenylalanine, L-tyrosine, and L-tryptophan.

It is an aspect of the present invention to provide a method for producing an L-amino acid comprising cultivating an Enterobacteriaceae bacterium that is able to produce an L-amino acid in a culture medium, and collecting the L-amino acid from the culture medium or the bacterium, wherein the bacterium has been modified to increase an activity of a protein which is able to confer to the bacterium resistance to growth inhibition by L-cysteine, wherein said protein is selected from the group consisting of:

(A) the protein of SEQ ID NO: 2, or a variant thereof, and (B) the protein of SEQ ID NO: 4, or a variant thereof.

It is a further aspect of the present invention to provide the method as described above, wherein expression of a DNA encoding said protein in said bacterium is enhanced.

It is a further aspect of the present invention to provide the method as described above, wherein said bacterium is transformed with a DNA encoding said protein.

It is a further aspect of the present invention to provide the method as described above, wherein the DNA comprises a gene selected from the group consisting of c0011 and d0663.

It is a further aspect of the present invention to provide the method as described above, wherein said protein is at least protein (B) or a variant thereof, and said bacterium has been further modified to increase expression of a DNA encoding the protein of SEQ ID NO: 6; or a variant thereof.

It is a further aspect of the present invention to provide the method as described above, wherein the DNA is the c09478 gene.

It is a further aspect of the present invention to provide the method as described above, wherein the bacterium belongs to the genus *Escherichia*.

It is a further aspect of the present invention to provide the method as described above, wherein the bacterium belongs to the genus *Pantoea*.

It is a further aspect of the present invention to provide the method as described above, wherein the bacterium is *Escherichia coli*.

It is a further aspect of the present invention to provide the method as described above, wherein the bacterium is *Pantoea ananatis*.

It is a further aspect of the present invention to provide the method as described above, wherein said L-amino acid is selected from the group consisting of an aromatic L-amino acid and a non-aromatic L-amino acid.

It is a further aspect of the present invention to provide the method as described above, wherein said aromatic L-amino acid is selected from the group consisting of L-phenylalanine, L-tyrosine, and L-tryptophan.

It is a further aspect of the present invention to provide the method as described above, wherein said non-aromatic L-amino acid is selected from the group consisting of L-threonine, L-lysine, L-cysteine and L-cysteine derivatives, L-methionine, L-leucine, L-isoleucine, L-valine, L-histidine, glycine, L-serine, L-alanine, L-asparagine, L-aspartic acid, L-glutamine, L-glutamic acid, L-proline, L-arginine and O-acetyl-L-serine.

It is a further aspect of the present invention to provide the method as described above, wherein said L-amino acid is selected from the group consisting of L-cysteine, L-valine, L-leucine, L-Isoleucine, L-threonine, L-glutamic acid, L-glycine, L-alanine, L-histidine, and O-acetyl-L-serine.

Methods embodying principles of the present invention are described in detail below.

BRIEF DESCRIPTION OF THE DRAWING FIGURES

Figure 1B:
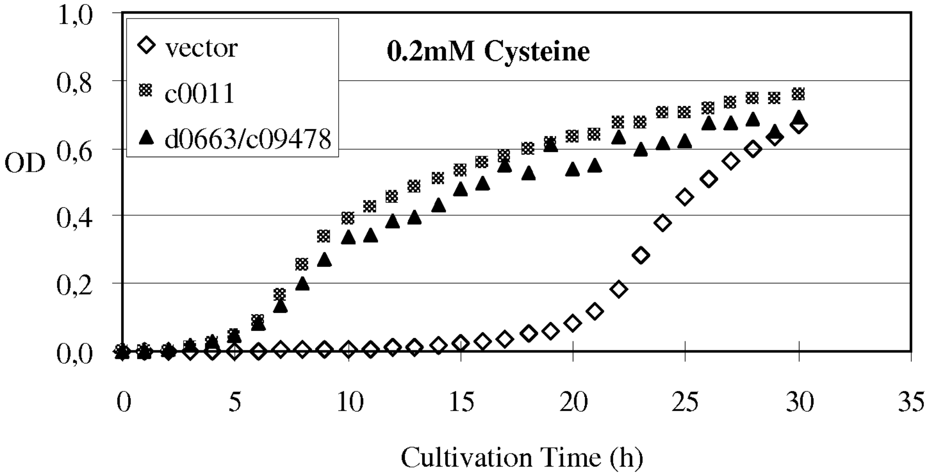

FIGS. 1A and 1B show growth curves of strains carrying the plasmids pSTV-c0011 PF and pSTV-PA36ccd in a medium containing cysteine.

DETAILED DESCRIPTION OF THE EXEMPLARY EMBODIMENTS

1. Bacterium

The bacterium can be an L-amino acid-producing bacterium of the Enterobacteriaceae family, wherein the bacterium has a protein derived from bacteria belonging to the genus *Pantoea*, and the protein is able to confer resistance to growth inhibition by L-cysteine.

The phrase "L-amino acid-producing bacterium" can mean a bacterium which has an ability to produce and excrete an L-amino acid into a medium, when the bacterium is cultured in the medium.

The phrase "L-amino acid-producing bacterium" can also mean a bacterium which is able to produce and cause accumulation of an L-amino acid in a culture medium in an amount larger than a wild-type or parental strain of *E. coli*, such as *E. coli* K-12, and preferably can mean that the microorganism is able to cause accumulation in a medium of an amount not less than 0.5 g/L, and in another embodiment not less than 1.0 g/L, of the target L-amino acid. The term "L-amino acid" can include L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, and O-acetyl-L-serine.

The term "aromatic L-amino acid" can include L-phenylalanine, L-tyrosine, and L-tryptophan. The term "non-aromatic L-amino acid" can include L-threonine, L-lysine, L-cysteine and L-cysteine derivatives, L-methionine, L-leucine, L-isoleucine, L-valine, L-histidine, glycine, L-serine, L-alanine, L-asparagine, L-aspartic acid, L-glutamine, L-glutamic acid, L-proline, L-arginine and O-acetyl-L-serine. L-threonine, L-lysine, L-cysteine, L-leucine, L-histidine, L-glutamic acid, L-phenylalanine, L-tryptophan, L-proline, L-arginine and O-acetyl-L-serine are other embodiments.

Some of the L-cysteine produced by the bacterium may change into L-cystine in the medium by the formation of a disulfide bond. S-sulfocysteine may be generated by the reaction of L-cysteine and thiosulfuric acid, which are both present in the medium (Szczepkowski T. W., Nature, vol. 182 (1958)). When S-sulfocysteine is produced in the medium, it can be converted into L-cysteine by reduction with a reducing agent such as dithiothreitol. Furthermore, the L-cysteine that is generated in the bacterial cells may be condensed with a ketone, aldehyde, or, for example, pyruvic acid, which is also present in the cells, to produce a thiazolidine derivative via the intermediate hemithioketal (refer to Japanese Patent No. 2992010). The thiazolidine derivative and hemithioketal may exist as an equilibrated mixture. When a thiazolidine derivative of L-cysteine is produced in the medium, L-cysteine can be produced by collecting the thiazolidine derivative from the medium to break the reaction equilibrium between the thiazolidine derivative and L-cysteine so that L-cysteine is produced in excess. Therefore, the L-cysteine-producing ability is not limited to the ability to accumulate only L-cysteine in the medium or cells, but also includes the ability to accumulate L-cystine or derivatives thereof such as S-sulfocysteine, a thiazolidine derivative, a hemithioketal, or a mixture thereof in the medium.

Some of the L-cysteine derivatives, such as γ-glutamylcysteine, glutathione, cystathionine, homocysteine, methionine, and S-adenosylmethionine, for example, can be biosynthesized from cysteine as an important starting material. The L-cysteine derivatives also can include methylcysteine, ethylcysteine, carbocysteine, sulfocysteine, acetylcysteine, and so forth. L-cysteine obtained as described above can be used to produce these L-cysteine derivatives.

Fermentative production of these compounds can be achieved by using the corresponding producer microorganisms as host strains with combinations of ability to overproduce cysteine. Therefore, the L-cysteine-producing ability includes the above compounds, such as γ-glutamylcysteine, glutathione, cystathionine, homocysteine, methionine, and S-denosylmethionine, which produce cysteine as an important intermediate.

To impart the ability to produce the compounds biosynthesized from cysteine such as γ-glutamylcysteine, glutathione, cystathionine, homocysteine, methionine and S-adenosylmethionine, methods conventionally employed in the breeding of coryneform bacteria or bacteria of the genus *Escherichia* (see "Amino Acid Fermentation", Gakkai Shuppan Center (Ltd.), 1st Edition, published May 30, 1986, pp. 77-100) can be used. Such methods include producing a microorganism having the properties of an auxotrophic mutant, an analogue-resistant strain, or a metabolic regulation mutant, or by constructing a recombinant strain so that it overexpresses a corresponding biosynthesis enzyme. Decreasing activities of enzymes that catalyze reactions which branch off the main pathway, and/or are involved in degradation of a corresponding compound or its intermediates, can also be effective to increase the product. Here, in the breeding of each producing bacteria, one or more of the above described properties may be imparted. The expression of corresponding biosynthesis enzyme(s) can be enhanced alone or in combinations of two or more. Furthermore, imparting properties such as an auxotrophic mutation, analogue resistance, or metabolic regulation mutation may be combined with the methods of enhancing the biosynthesis enzymes.

The phrase "bacterium which has a resistance to growth inhibition by L-cysteine" can mean a bacterium derived from a strain of bacterium as the parent strain, and which has genetic properties so that it can grow in a medium containing L-cysteine. A solid medium can be used.

The bacterium which is resistant to growth inhibition by L-cysteine shows better favorable growth as compared with the parent strain when cultured in a medium containing L-cysteine. For example, a bacterium which can form colonies within 20 hours of cultivation at 34° C. on plates with M9 minimal medium containing 50 M or more, or in another example 200 μM of L-cysteine, can be resistant to L-cysteine.

The strains carrying the genes as described above which can grow faster than the control strain in a medium containing 50 M L-cysteine, or in another example 200 M, indicates that this gene or gene locus can confer cysteine resistance.

The Enterobacteriaceae family includes bacteria belonging to the genera *Escherichia, Enterobacter, Erwinia, Klebsiella, Pantoea, Photorhabdus, Providencia, Salmonella, Serratia, Shigella, Morganella, Yersinia*, etc. Specifically, those classified into the Enterobacteriaceae according to the taxonomy used by the NCBI (National Center for Biotechnology Information) database (www.ncbi.nlm.nih.gov/Taxonomy/Browser/wwwtax.cgi?id=91347) can be used. A bacterium belonging to the genus *Escherichia* or *Pantoea* can be used.

The phrase "a bacterium belonging to the genus *Escherichia*" can mean that the bacterium is classified into the genus *Escherichia* according to the classification known to a person skilled in the art of microbiology. Examples of a bacterium belonging to the genus *Escherichia* can include, but are not limited to, *Escherichia coli* (*E. coli*).

The bacterium belonging to the genus *Escherichia* is not particularly limited, however for example, bacteria described by Neidhardt, F. C. et al. (*Escherichia coli* and *Salmonella typhimurium*, American Society for Microbiology, Washington D.C., 1208, Table 1) can be used.

The phrase "a bacterium belonging to the genus *Pantoea*" can mean that the bacterium is classified as the genus *Pantoea* according to the classification known to a person skilled in the art of microbiology. Some species of *Enterobacter agglomerans* have been recently re-classified into *Pantoea agglomerans, Pantoea ananatis, Pantoea stewartii* or the like, based on nucleotide sequence analysis of 16S rRNA, etc (International Journal of Systematic Bacteriology, July 1989, 39(3). p. 337-345). Furthermore, some bacteria belonging to the genus *Erwinia* were re-classified as *Pantoea ananatis* or *Pantoea stewartii* (International Journal of Systematic Bacteriology, January 1993, 43(1), pp. 162-173). Typical strains of the *Pantoea* bacteria include, but are not limited to, *Pantoea ananatis, Pantoea stewartii, Pantoea agglomerans*, and *Pantoea citrea*. Specific examples include the following strains: *Pantoea ananatis* AJ13355 (FERM BP-6614, European Patent Publication No. 0952221), *Pantoea ananatis* AJ13356 (FERM BP-6615, European Patent Publication No. 0952221), *Pantoea ananatis* AJ 13601 (FERM BP-7207, European Patent Publication No. 0952221), *Pantoea ananatis* SC17 (FERM BP-11091, European Patent Publication No. 0952221). An exemplary λ-Red resistant strain is *Pantoea ananatis* SC17(0) (VKPM B-9246, RU application 2006134574). The SC17 strain was deposited at the National Institute of Advanced Industrial Science and Technology, International Patent Organism Depository (address: Tsukuba Central 6, 1-1, Higashi 1-Chome, Tsukuba-shi, Ibaraki-ken, 305-8566, Japan) on Feb. 4, 2009 under the Budapest Treaty, and assigned an accession number of FERM BP-11091. The SC17(O) strain was deposited at the Russian National Collection of Industrial Microorganisms (VKPM), GNII Genetika (address: Russia, 117545 Moscow, 1 Dorozhny proezd. 1) on Sep. 21, 2005 with an accession number of VKPM B-9246, and then converted to international deposit under the Budapest Treaty on Oct. 13, 2006.

According to the presently disclosed subject matter, a bacterium of Enterobacteriaceae family is modified to increase an activity of the protein having the amino acid sequence of SEQ ID NO: 2 or its variant, or the protein having the amino acid sequence of SEQ ID NO: 4, or its variant, or activities of both of these proteins.

In an embodiment of the presently disclosed subject matter, when the bacterium has been modified to increase at least the protein having the amino acid sequence of SEQ ID NO: 4, or its variant, the bacterium is further modified to increase expression of a DNA encoding the protein of SEQ ID NO: 6, or its variant.

Examples of the protein which has the amino acid sequence of SEQ ID NO: 2 or its variant include the c0011 gene. Examples of the protein which has the amino acid sequence of SEQ ID NO: 4 or its variant include the c0663 gene. Examples of the protein which has the amino acid sequence of SEQ ID NO: 6 or its variant include the c09478 gene.

The nucleotide sequence of the c0011 gene from the strain *P. ananatis* SC17 and the amino acid sequence of protein encoded by the c0011 gene are shown in SEQ ID NO: 1 and SEQ ID NO: 2, respectively.

The nucleotide sequence of the d0663 gene from the strain *P. ananatis* SC17 and the amino acid sequence of protein encoded by the d0663 gene are shown in SEQ ID NO: 3 and SEQ ID NO: 4, respectively.

The nucleotide sequence of the c09478 gene from the strain *P ananatis* SC17 and the amino acid sequence of protein encoded by the c09478 gene are shown in SEQ ID NO: 5 and SEQ ID NO: 6, respectively.

Since there may be some differences in DNA sequences between the genera or strains of the Enterobacteriaceae family, the c0011, d0663 and c09478 genes are not limited to the genes shown in SEQ ID No:1, SEQ ID No:3 and SEQ ID No:5 but may include genes homologous to SEQ ID No:1, SEQ ID No:3 and SEQ ID No:5.

The c0011 gene may encode the putative transmembrane protein of *Klebsiella pneumoniae* (GenBank Accession No. ABR77369.1), hypothetical protein KCO_01469 of *Citrobacter koseri* (GenBank Accession No. ABV12602.1), Permease (DMT) superfamily of *Acinetobacter baumannii* (GenBank Accession No. ABO12139.2), and putative membrane protein of *Pseudomonas aeruginosa* (GenBank Accession No. ABR86455.1).

The d0663 gene may encode the Lysine exporter protein (LYSE/YGGA) of *Erwinia tasmaniensis* (GenBank Accession No. CAO95150.1), putative membrane protein of *Pectobacterium atrosepticum* (GenBank Accession No. CAG76207.1), probable transport protein of *Chromobacterium violaceum* (GenBank Accession No. AAQ59575.1), and Lysine exporter protein (LYSE/YGGA) of *Burkholderia vietnamiensis* (GenBank Accession No. ABO58107.1).

Therefore, the protein variant encoded by the c0011, d0663, and c09478 genes can have a homology of not less than 80%, in another example not less than 90%, in another example not less than 95%, or in another example not less than 98%, and in another example not less than 99%, with respect to the entire amino acid sequences shown in SEQ ID No:2, SEQ ID No:4, and SEQ ID No:6, respectively, as long as the protein confers resistance to cysteine. The phrase "protein variant" can mean proteins which have changes in their sequences, whether these changes are deletions, insertions, additions, or substitutions of amino acids. The number of changes in the variant proteins depends on the position in the three dimensional structure of the protein or the type of amino acid residues. It may be 1 to 30, in another example 1 to 15, and in another example 1 to 5 in SEQ ID No:2, SEQ ID No:4 and SEQ ID No:6. These changes in the variants can occur in regions of the protein which are not critical for the three dimensional structure of the protein. This is because some amino acids have high homology to one another so the three dimensional structure is not affected by such a change.

Homology between two amino acid sequences can be determined using well-known methods, for example, the computer program BLAST 2.0, which calculates three parameters: score, identity and similarity. In this specification, "homology" can mean "identity".

The substitution, deletion, insertion, or addition of one or several amino acid residues can be conservative mutation(s) so that the activity is maintained. A representative conservative mutation can be a conservative substitution. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

Therefore, the c0011, d0663 and c09478 genes may be variants which hybridize under stringent conditions with the nucleotide sequences shown in SEQ ID No: 1, SEQ ID No:3 and SEQ ID No:5, respectively, or probes which can be prepared from these nucleotide sequences, provided that a functional protein is encoded. "Stringent conditions" include those under which a specific hybrid, for example, a hybrid having homology of not less than 60%, and in another example not less than 70%, and in another example not less than 80%, and in another example not less than 90%, and in another example not less than 95%, and in another example not less than 98%, and in yet another example not less than 99%, is formed and a non-specific hybrid, for example, a hybrid having homology lower than the above, is not formed. For example, stringent conditions are exemplified by washing one time or more, and in another example two or three times, at a salt concentration of 1×SSC, 0.1% SDS, and in another example 0.1×SSC, 0.1%, at 60° C. Duration of washing depends on the type of membrane used for blotting and, as a rule, should be what is recommended by the manufacturer. For example, the recommended duration of washing for the Hybond™ N+ nylon membrane (Amersham) under stringent conditions is 15 minutes. Washing can be performed 2 to 3 times. The length of the probe may be suitably selected depending on the hybridization conditions, and can be 100 bp to 1 kbp.

The phrase "a bacterium has been modified to increase an activity of a protein" means that the activity of the protein in the cell is higher as compared to the non-modified microorganism, for example, a parental or wild-type strain. The activity of the protein can be increased in the cell by enhancing the expression of the gene encoding the protein. Examples of such modification can include increasing the copy number of expressed gene per cell, increasing the expression level of the gene, and so forth. The quantity of the copy number of an expressed gene can be measured, for example, by restricting the chromosomal DNA followed by Southern blotting using a probe based on the gene sequence, fluorescence in situ hybridization (FISH), and the like. The level of gene expression can be measured by various known methods including Northern blotting, quantitative RT-PCR, and the like.

More concretely, enhancing the expression of the c0011, d0663 or c09478 gene can be attained by increasing the copy number of the c0011, d0663 or c09478 gene, modifying an expression regulatory sequence of the c0011, d0663 or c09478 gene, amplifying a gene encoding a regulatory factor that is responsible for increasing expression of the c0011, d0663 or c09478 genes, respectively, or disrupting or attenuating a gene encoding a regulatory factor that is responsible for reducing expression of the c0011, d0663 or c09478 gene, respectively, by using a transformation or a homologous recombination technique.

For example, a recombinant DNA can be prepared by ligating a gene fragment containing the c0011, d0663 or c09478 gene to a vector, preferably a multi-copy vector, which can replicate in the host microorganism, and introducing the resulting vector into the host microorganism.

The copy number of the c0011, d0663 or c09478 gene can also be increased by integrating multiple copies of the gene into a chromosomal DNA of a microorganism. In order to integrate multiple copies of the c0011, d0663 or c09478 gene into a chromosomal DNA of a microorganism, homologous recombination can be performed by targeting a sequence which exists in multiple copies on a chromosomal DNA. Repetitive DNA and inverted repeats at the end of a transposon can be used. Alternatively, as disclosed in JP2-109985A, it is also possible to incorporate the c0011, d0663 or c09478 gene into a transposon, and allow it to be transferred so that multiple copies of the gene are integrated into the chromosomal DNA. Integration of the c0011, d0663 or c09478 gene into the chromosome can be confirmed by southern hybridization using a probe having a partial sequence of the c0011, d0663 or c09478 genes.

Enhancing expression of the c0011, d0663 or c09478 gene can also be attained by replacing an expression regulatory sequence, including a promoter of the c0011, d0663 or c09478 gene, on a chromosomal DNA or on a plasmid, with a stronger one, as described in WO 00/18935. For example, the lac promoter, trp promoter, trc promoter, $P_L$ promoter, and so forth are known as strong promoters. Moreover, it is also possible to introduce several nucleotide substitutions into a promoter region for the c0011, d0663 or c09478 gene so that the promoter is stronger. A method for evaluating the strength of promoters and examples of strong promoters are disclosed in Goldstein et al. (Prokaryotic promoters in biotechnology. Biotechnol. Annu. Rev., 1995, 1, 105-128). Furthermore, it is known that a spacer sequence between the ribosome binding site (RBS) and translation initiation codon, especially, several nucleotides just upstream of the initiation codon, has a great influence on translation efficiency. Therefore, this sequence may be modified. Expression regulatory sequences of the c0011, d0663 and c09478 genes may be identified using a vector for promoter identification or genetic analysis software such as GENETYX. Expression can also be improved by prolonging the lifetime of the mRNA. Furthermore, enzyme activity can also be increased by preventing degradation of the enzyme protein.

In order to enhance an activity of the protein encoded by the c0011, d0663 or c09478 gene, a mutation which increases an L-amino acid-export ability may be introduced into the c0011, d0663 or c09478 gene. Examples of mutations that increase activity of the protein encoded by the c0011, d0663 or c09478 gene (C0011, D0663 or C09478 protein) include a promoter sequence mutation that increases the transcription of the c0011, d0663 or c09478 genes, and a c0011, d0663 or c09478 gene coding region mutation that increases the specific activity of the C0011, D0663 or C09478 protein.

Methods for preparation of plasmid DNA, digestion and ligation of DNA, transformation, selection of an oligonucleotide as a primer, and the like may be typical methods well-known to one skilled in the art. These methods are described, for instance, in Sambrook, J., Fritsch, E. F., and Maniatis, T., "Molecular Cloning: A Laboratory Manual, Second Edition", Cold Spring Harbor Laboratory Press (1989).

L-Amino Acid-Producing Bacteria

Bacteria which are able to produce either an aromatic or a non-aromatic L-amino acids may be used.

The bacterium can be obtained by introducing a gene which encodes a protein able to confer resistance to cysteine in a bacterium which inherently has the ability to produce L-amino acids. Alternatively, the bacterium can be obtained by imparting the ability to produce L-amino acids to a bacterium that already has a protein able to confer resistance to cysteine.

L-Threonine-Producing Bacteria

Examples of parent strains which can be used to derive L-threonine-producing bacteria include, but are not limited to, strains belonging to the genus *Escherichia*, such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and the like.

The strain TDH-6 is deficient in the thrC gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain B-3996 was deposited on Nov. 19, 1987 in the All-Union Scientific Center of Antibiotics (Russia, 117105 Moscow, Nagatinskaya Street 3-A) under the accession number RIA 1867. The strain was also deposited in the Russian National Collection of Industrial Microorganisms (VKPM) (Russia, 117545 Moscow, $1^{st}$ Dorozhny proezd, 1) on Apr. 7, 1987 under the accession number B-3996.

*E. coli* VKPM B-5318 (EP 0593792B) may also be used as a parent strain to derive L-threonine-producing bacteria of the present invention. The strain B-5318 is prototrophic with regard to isoleucine and a temperature-sensitive lambda-phage C1 repressor and PR promoter replaces the regulatory region of the threonine operon in plasmid pVIC40. The strain VKPM B-5318 was deposited in the Russian National Collection of Industrial Microorganisms (VKPM) on May 3, 1990 under accession number of VKPM B-5318.

The bacterium can be additionally modified to enhance expression of one or more of the following genes:

the mutant thrA gene which codes for aspartokinase homoserine dehydrogenase I resistant to feed back inhibition by threonine;

the thrB gene which codes for homoserine kinase;

the thrC gene which codes for threonine synthase;

the rhtA gene which codes for a putative transmembrane protein;

the asd gene which codes for aspartate-(3-semialdehyde dehydrogenase; and the aspC gene which codes for aspartate aminotransferase (aspartate transaminase);

The thrA gene which encodes aspartokinase homoserine dehydrogenase I of *Escherichia coli* has been elucidated (nucleotide positions 337 to 2799, GenBank accession no. NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide positions 2801 to 3733, GenBank accession no. NC_000913.2, gi: 49175990). The thrB gene is located between the thrA and thrC genes on the chromosome of *E. coli* K-12. The thrC gene which encodes threonine synthase of *Escherichia coli* has been elucidated (nucleotide positions 3734 to 5020, GenBank accession no. NC_000913.2, gi: 49175990). The thrC gene is located between the thrB gene and the yaaX open reading frame on the chromosome of *E. coli* K-12. All three genes function as a single threonine operon. To enhance expression of the threonine operon, the attenuator region which affects the transcription can be removed from the operon (WO 2005/049808, WO 2003/097839).

A mutant thrA gene which codes for aspartokinase homoserine dehydrogenase I resistant to feed back inhibition by threonine, as well as the thrB and thrC genes, can be obtained as one operon from the well-known plasmid pVIC40 which is present in the threonine producing *E. coli* strain VKPM B-3996. Plasmid pVIC40 is described in detail in U.S. Pat. No. 5,705,371.

The rhtA gene exists at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi:440181) and located between the pexB and ompX genes. The unit expressing a protein encoded by the ORF1 has been designated the rhtA gene (rht: resistance to homoserine and threonine). Also, it was revealed that the rhtA23 mutation is an A-for-G substitution at position −1 with respect to the ATG start codon (ABSTRACTS of the 17$^{th}$ International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide positions 3572511 to 3571408, GenBank accession no. NC_000913.1, gi:16131307), and can be obtained by PCR (polymerase chain reaction; refer to White, T. J. et al., Trends Genet., 5, 185 (1989)) utilizing primers prepared based on the nucleotide sequence of the gene. The asd genes of other microorganisms can be obtained in a similar manner.

Also, the aspC gene of *E. coli* has already been elucidated (nucleotide positions 983742 to 984932, GenBank accession no. NC_000913.1, gi:16128895), and can be obtained by PCR. The aspC genes of other microorganisms can be obtained in a similar manner.

L-Lysine-Producing Bacteria

Examples of L-lysine-producing bacteria belonging to the genus *Escherichia* include mutants having resistance to an L-lysine analogue. The L-lysine analogue inhibits growth of bacteria belonging to the genus *Escherichia*, but this inhibition is fully or partially desensitized when L-lysine is present in a medium. Examples of the L-lysine analogue include, but are not limited to, oxalysine, lysine hydroxamate, S-(2-aminoethyl)-L-cysteine (AEC), γ-methyllysine, α-chlorocaprolactam, and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The strain WC196 may be used as an L-lysine producing bacterium of *Escherichia coli*. This bacterial strain was bred by conferring AEC resistance to the strain W3110, which was derived from *Escherichia coli* K-12. The resulting strain was designated *Escherichia coli* AJ13069 strain and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of parent strains which can be used to derive L-lysine-producing bacteria also include strains in which expression of one or more genes encoding an L-lysine biosynthetic enzyme are enhanced. Examples of such genes include, but are not limited to, genes encoding dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenase (asd), and aspartase (aspA) (EP 1253195 A). In addition, the parent strains may have increased expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations thereof.

Examples of parent strains which can be used to derive L-lysine-producing bacteria also include strains having decreased or eliminated activity of an enzyme that catalyzes a reaction which generates a compound other than L-lysine by branching off from the biosynthetic pathway of L-lysine. Examples of such enzymes include homoserine dehydrogenase, lysine decarboxylase (U.S. Pat. No. 5,827,698), and the malic enzyme (WO 2005/010175).

L-Cysteine-Producing Bacteria

Examples of parent strains which can be used to derive L-cysteine-producing bacteria include, but are not limited to, strains belonging to the genus *Escherichia*, such as *E. coli* JM15 which is transformed with different cysE alleles coding for feedback-resistant serine acetyltransferases (U.S. Pat. No. 6,218,168, Russian patent application 2003121601); *E. coli* W3110 having over-expressed genes which encode proteins suitable for secreting substances toxic for cells (U.S. Pat. No. 5,972,663); *E. coli* strains having lowered cysteine desulfhydrase activity (JP11155571A2); *E. coli* W3110 with increased activity of a positive transcriptional regulator for cysteine regulon encoded by the cysB gene (WOO 127307A1), and the like.

Bacteria Producing L-Cysteine Derivatives.

Examples of parent strains which can be used to derive bacteria producing L-cysteine derivatives include, but are not limited to, the strains described below. The ability to produce γ-glutamylcysteine can be achieved, for example, by enhancing activity of γ-glutamylcysteine synthetase and/or decreasing activity of glutathione synthetase. The ability to produce glutathione can be achieved by enhancing activity of γ-glutamylcysteine synthetase and/or glutathione synthetase. Using mutant γ-glutamylcysteine synthetases that are not subject to feed-back inhibition by glutathione can also confer and/or improve ability to produce glutathione. Methods for microbial production of glutathione are summarized in Yin et al. (Yin Li, Gongyuan Wei, Jian Chen. Appl Microbiol Biotechnol (2004) 66: 233-242). The ability to produce methionine can be achieved by conferring L-threonine auxotroph or norleucine resistance (Japanese Patent Laid-open No. 2000-139471). Inactivation of methionine repressor and/or enhancement of methionine biosynthetic pathway (i.e., homoserine O-succinyltransferase and cystathionine γ-synthase) can be also effective on conferring and improving the ability to produce methionine (Japanese Patent Laid-open No. 2000-139471). Furthermore, using mutant homoserine O-succinyltransferases that are not subject to feed-back inhibition by methionine can also confer and/or improve the ability to produce methionine. Since cystathionine and homocysteine are intermediates of methionine biosynthesis, part of the methods for producing methionine described above can be applied for their production. Specific examples for improving cystathionine production are described in Japanese Patent Laid-open No. 2003-010654 (utilization of methionine auxotroph) and Japanese Patent Laid-open No. 2005-16842 (supplement of cysteine or homoserine in the productive media). Since cystathionine is a precursor of homocysteine, these methods can be applied to homocysteine production. The ability to produce S-adenosylmethionine can be achieved by enhancing methionine adenosyltransferase (European Pat. No. 0647712, European Pat. No. 1457569) and/or efflux pump MdfA (U.S. Pat. No. 7,410,789).

L-Leucine-Producing Bacteria

Examples of parent strains which can be used to derive L-leucine-producing bacteria include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (JP 62-34397 B and JP 8-70879 A); *E. coli* strains obtained by the gene engineering method described in WO 96/06926; *E. coli* H-9068 (JP 8-70879 A), and the like.

The bacterium may be improved by enhancing the expression of one or more genes involved in L-leucine biosynthesis. Examples include genes of the leuABCD operon, which are preferably represented by a mutant leuA gene coding for isopropylmalate synthase which is not subject to feedback inhibition by L-leucine (U.S. Pat. No. 6,403,342). In addition, the bacterium may be improved by enhancing the expression of one or more genes coding for proteins which are responsible for secretion of L-amino acids from the bacterial cell. Examples of such genes include the b2682 and b2683 genes (ygaZH genes) (EP 1239041 A2).

L-Histidine-Producing Bacteria

Examples of parent strains which can be used to derive L-histidine-producing bacteria include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); *E. coli* AI80/pFM201 (U.S. Pat. No. 6,258,554) and the like.

Examples of parent strains which can be used to derive L-histidine-producing bacteria also include strains in which expression of one or more genes encoding an L-histidine biosynthetic enzyme are enhanced. Examples of such genes include genes encoding ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore an L-histidine-producing ability can also be efficiently enhanced by introducing a mutation into ATP phosphoribosyltransferase which imparts resistance to the feedback inhibition (Russian Patent Nos. 2003677 and 2119536).

Specific examples of strains having an L-histidine-producing ability include *E. coli* FERM-P 5038 and 5048 which have been transformed by a vector carrying a DNA encoding an L-histidine-biosynthetic enzyme (JP 56-005099 A), *E. coli* strains transformed with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-Glutamic Acid-Producing Bacteria

Examples of parent strains which can be used to derive L-glutamic acid-producing bacteria include, but are not limited to, strains belonging to the genus *Escherichia*, such as *E. coli* VL334thrC$^+$ (EP 1172433). *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 which was grown on wild-type *E. coli* K12 (VKPM B-7) cells. As a result, an L-isoleucine auxotrophic strain VL334thrC$^+$ (VKPM B-8961), which is able to produce L-glutamic acid, was obtained.

Examples of parent strains which can be used to derive L-glutamic acid-producing bacteria include, but are not limited to, strains which are deficient in α-ketoglutarate dehydrogenase activity, or strains in which one or more genes encoding an L-glutamic acid biosynthetic enzyme are enhanced. Examples of the genes involved in L-glutamic acid biosynthesis include genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgml), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), and glucose phosphate isomerase (pgi).

Examples of strains which have been modified so that expression of the citrate synthetase gene, the phosphoenolpyruvate carboxylase gene, and/or the glutamate dehydrogenase gene is/are enhanced include those disclosed in EP1078989A, EP955368A, and EP952221A.

Examples of strains which have been modified so that expression of the citrate synthetase gene and/or the phosphoenolpyruvate carboxylase gene are reduced, and/or are deficient in α-ketoglutarate dehydrogenase activity include those disclosed in EP1078989A, EP955368A, and EP952221A.

Examples of parent strains which can be used to derive the L-glutamic acid-producing bacteria also include strains having decreased or eliminated activity of an enzyme that catalyzes synthesis of a compound other than L-glutamic acid by branching off from an L-glutamic acid biosynthesis pathway. Examples of such enzymes include isocitrate lyase (aceA), c-ketoglutarate dehydrogenase (sucA), phosphotransacetylase (pta), acetate kinase (ack), acetohydroxy acid synthase (ilvG), acetolactate synthase (ilyl), formate acetyltransferase (pfl), lactate dehydrogenase (ldh), and glutamate decarboxylase (gadAB). Bacteria belonging to the genus *Escherichia* deficient in the α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

*E. coli* W3110sucA::$Km^R$

*E. coli* AJ12624 (FERM BP-3853)

*E. coli* AJ12628 (FERM BP-3854)

*E. coli* AJ12949 (FERM BP-4881)

*E. coli* W3110sucA::$Km^R$ is a strain obtained by disrupting the α-ketoglutarate dehydrogenase gene (hereinafter referred to as "sucA gene") of *E. coli* W3110. This strain is completely deficient in the α-ketoglutarate dehydrogenase.

Other examples of L-glutamic acid-producing bacterium include those which belong to the genus *Escherichia* and have resistance to an aspartic acid antimetabolite. These strains can also be deficient in the α-ketoglutarate dehydrogenase activity and include, for example, *E. coli* AJ13199 (FERM BP-5807) (U.S. Pat. No. 5,908,768), FFRM P-12379, which additionally has a low L-glutamic acid decomposing ability (U.S. Pat. No. 5,393,671); AJ13138 (FERM BP-5565) (U.S. Pat. No. 6,110,714), and the like.

Examples of L-glutamic acid-producing bacteria include mutant strains belonging to the genus *Pantoea* which are deficient in the α-ketoglutarate dehydrogenase activity or have a decreased α-ketoglutarate dehydrogenase activity, and can be obtained as described above. Such strains include *Pantoea ananatis* AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of Budapest Treaty on Jan. 11, 1999 and received an accession number of FERM BP-6615. *Pantoea ananatis* AJ13356 is deficient in the α-ketoglutarate dehydrogenase activity as a result of disruption of the αKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis.*

L-Phenylalanine-Producing Bacteria

Examples of parent strains which can be used to derive L-phenylalanine-producing bacteria include, but are not limited to, strains belonging to the genus *Escherichia*, such as *E. coli* AJ12739 (tyrA::Tn10, tyrR) (VKPM B-8197); *E. coli* HW1089 (ATCC 55371) harboring the mutant pheA34 gene (U.S. Pat. No. 5,354,672); *E. coli* MWEC101-b (KR8903681); *E. coli* NRRL B-12141, NRRL B-12145, NRRL B-12146 and NRRL B-12147 (U.S. Pat. No. 4,407, 952). Also, as a parent strain, *E. coli* K-12 [W3110 (tyrA)/pPHAB (FERM BP-3566), *E. coli* K-12 [W3110 (tyrA)/pPHAD](FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ 12604 (FERM BP-3579) may be used (EP 488424 B1). Furthermore, L-phenylalanine producing bacteria belonging to the genus *Escherichia* with an enhanced activity of the protein encoded by the yedA gene or the yddG gene may also be used (U.S. patent application publication nos. 2003/0148473 A1 and 2003/0157667 A1).

L-Tryptophan-Producing Bacteria

Examples of parent strains which can be used to derive the L-tryptophan-producing bacteria include, but are not limited to, strains belonging to the genus *Escherichia*, such as *E. coli* JP4735/pMU3028 (DSM10122) and JP6015/pMU91 (DSM10123) which is deficient in the tryptophanyl-tRNA synthetase encoded by mutant trpS gene (U.S. Pat. No. 5,756, 345); *E. coli* SV164 (pGH5) having a serA allele encoding phosphoglycerate dehydrogenase free from feedback inhibition by serine and a trpE allele encoding anthranilate synthase free from feedback inhibition by tryptophan (U.S. Pat. No. 6,180,373); *E. coli* AGX17 (pGX44) (NRRL B-12263) and AGX6(pGX50)aroP (NRRL B-12264) deficient in the enzyme tryptophanase (U.S. Pat. No. 4,371,614); *E. coli* AGX17/pGX50,pACKG4-pps in which a phosphoenolpyruvate-producing ability is enhanced (WO 97/08333, U.S. Pat. No. 6,319,696), and the like may be used. L-tryptophan-producing bacteria belonging to the genus *Escherichia* with an enhanced activity of the identified protein encoded by and the yedA gene or the yddG gene may also be used (U.S. patent application publication nos. 2003/0148473 A1 and 2003/0157667 A1).

Examples of parent strains which can be used to derive the L-tryptophan-producing bacteria also include strains in which one or more activities of the enzymes selected from anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, so that a mutation desensitizing the feedback inhibition may be introduced into these enzymes. Specific examples of strains having such a mutation include a *E. coli* SV164 which harbors desensitized anthranilate synthase and a transformant strain obtained by introducing into the *E. coli* SV164 the plasmid pGH5 (WO 94/08031), which contains a mutant serA gene encoding feedback-desensitized phosphoglycerate dehydrogenase.

Examples of parent strains which can be used to derive the L-tryptophan-producing bacteria also include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase includes α and β subunits which are encoded by the trpA and trpB genes, respectively. In addition, L-tryptophan-producing ability may be improved by enhancing expression of the isocitrate lyase-malate synthase operon (WO 2005/103275).

L-Proline-Producing Bacteria

Examples of parent strains which can be used to derive L-proline-producing bacteria include, but are not limited to, strains belonging to the genus *Escherichia*, such as *E. coli* 702ilvA (VKPM B-8012) which is deficient in the ilvA gene and is able to produce L-proline (EP 1172433). The bacterium may be improved by enhancing the expression of one or more genes involved in L-proline biosynthesis. Examples of such genes for L-proline producing bacteria which are preferred include the proB gene coding for glutamate kinase of which feedback inhibition by L-proline is desensitized (DE Patent 3127361). In addition, the bacterium may be improved by enhancing the expression of one or more genes coding for proteins excreting L-amino acid from bacterial cell. Such genes are exemplified by the b2682 and b2683 genes (ygaZH genes) (EP1239041 A2).

Examples of bacteria belonging to the genus *Escherichia*, which have an activity to produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The $15^{th}$ Miami winter symposium, 1983, p. 34), and the like.

L-Arginine-Producing Bacteria

Examples of parent strains which can be used to derive L-arginine-producing bacteria include, but are not limited to, strains belonging to the genus *Escherichia*, such as *E. coli* strain 237 (VKPM B-7925) (U.S. Patent Application Publication No. 2002/058315 A1) and its derivative strains harboring mutant N-acetylglutamate synthase (Russian Patent Application No. 2001112869), *E. coli* strain 382 (VKPM B-7926) (EP1170358A1), an arginine-producing strain into which argA gene encoding N-acetylglutamate synthetase is introduced therein (EP1170361A1), and the like.

Examples of parent strains which can be used to derive L-arginine producing bacteria also include strains in which expression of one or more genes encoding an L-arginine biosynthetic enzyme are enhanced. Examples of such genes include genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-Valine-Producing Bacteria

Examples of parent strains which can be used to derive L-valine-producing bacteria include bacteria belonging to the genus *Escherichia* such as H-81 (VKPM B-8066), NRRL B-12287 and NRRL B-12288 (U.S. Pat. No. 4,391,907), VKPM B-4411 (U.S. Pat. No. 5,658,766), VKPM B-7707 (European patent application EP1016710A2), or the like.

Example of parent strains which can be used to derive L-valine-producing bacteria include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by the L-valine that is produced. Furthermore, the ilvA gene in the operon can be disrupted so that threonine deaminase activity is decreased.

Examples of parent strains which can be used to derive L-valine-producing bacteria also include mutants having a mutation of amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM) (Russia, 117545 Moscow, $1^{st}$ Dorozhny Proezd, 1) on Jun. 24, 1988 under accession number VKPM B-4411.

Furthermore, mutants requiring lipoic acid for growth and/or lacking $H^+$-ATPase can also be used as parent strains (WO 96/06926).

L-Isoleucine-Producing Bacteria

Examples of parent strains which can be used to derive L-isoleucine producing bacteria include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parent strains (JP 2-458 A, FR 0356739, and U.S. Pat. No. 5,998,178).

L-Tyrosine-Producing Bacteria

Examples of tyrosine-producing bacteria include *Escherichia* bacteria with a desensitized prephenate dehydratase gene (tyrA). The expression product of this gene is desensitized to inhibition by tyrosine (European Patent Application Laid-open No. 1616940).

2. Method for producing L-amino acid

A method is described for producing an L-amino acid by cultivating a bacterium as described herein in a culture medium to produce and excrete the L-amino acid into the medium, and collecting the L-amino acid from the medium.

The cultivation, collection, and purification of an L-amino acid from the medium and the like may be performed in a manner similar to conventional fermentation methods wherein an amino acid is produced using a bacterium.

The medium used for culture may be either a synthetic or natural medium, so long as the medium includes a carbon source and a nitrogen source and minerals and, if necessary, appropriate amounts of nutrients which the bacterium requires for growth. As the carbon source, saccharides such as glucose, fructose, sucrose, molasses and starch hydrolysate, and organic acids such as fumaric acid, citric acid and succinic acid, alcohol cuahc as ethanol and glycerol, can be used. As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation can be performed under aerobic conditions, such as by shaking and/or stirring with aeration, at a temperature of 20 to 40° C., or in another example 30 to 38° C. The pH of the culture is usually between 5 and 9, or in another example between 6.5 and 7.2. The pH of the culture can be adjusted with ammonia, calcium carbonate, various acids, various bases, and buffers. Usually, a 1 to 5-day cultivation leads to accumulation of the target L-amino acid in the liquid medium.

After cultivation, solids such as cells can be removed from the liquid medium by centrifugation or membrane filtration, and then the L-amino acid can be collected and purified by ion-exchange (Nagai, H. et al., Separation Science and Technology, 39(16), 3691-3710), concentration, membrane separation method (Japanese Patent Laid-open Nos. 9-164323 and 9-173792), crystallization methods (WO 2008/078448, WO 2008/078646), and/or other methods.

The L-amino acid collected can contain bacterial cells, medium components, moisture, and by-product metabolites of the microorganism in addition to the L-amino acid. Purity of the collected L-amino acid is, for example, 50% or higher, 85% or higher, or even 95% or higher (U.S. Pat. No. 5,431,933, Japanese Patent Publication No. 1-214636, U.S. Pat. Nos. 4,956,471, 4,777,051, 4,946,654, 5,840,358, 6,238,714, U.S. Patent Application Publication No. 2005/0025878).

L-Cysteine obtained as described above can be used for production of L-cysteine derivatives. The L-cysteine derivatives include methylcysteine, ethylcysteine, carbocisteine, sulfocysteine, acetylcysteine, and so forth.

Furthermore, when a thiazolidine derivative of L-cysteine is accumulated in the medium, L-cysteine can be produced by changing the reaction equilibrium between the thiazolidine derivative and L-cysteine to the L-cysteine side. Furthermore, when S-sulfocysteine is accumulated in the medium, it can be converted into L-cysteine by reduction using a reducing agent such as dithiothreitol.

EXAMPLES

The present invention will be more concretely explained below with reference to the following non-limiting examples.

Example 1

Over-Expression of Each of a Gene c0011 and a Gene Locus d0663-c09478

1-1. Cloning of c0011 Gene from *P. Ananatis* SC17.

A DNA fragment containing approximate 300 nt upstream and 200 nt downstream of c0011ORF was obtained by PCR from genomic DNA of *P. ananatis* SC17 using primers P1 (SEQ ID NO: 7) and P2 (SEQ ID NO: 8) with PrimeSTAR DNA polymerase (Takara Bio Inc.) (5 sec at 98° C., 10 sec at 55° C., 4 min at 72° C. for 30 cycles after 5 min at 94° C.).

The obtained 1.4 kb DNA fragment was cloned into a plasmid pSTV29 (Takara Bio Inc.) using BamHI sites designed at the 5' end of each primer to obtain the plasmid pSTV-c0011 PF, in which c0011 gene was oriented in the same direction as the lacZ promoter located on pSTV29.

1-2. Cloning of d0663-c09478 Gene Locus from *P. Ananatis* SC17.

A DNA fragment containing approximate 200 nt downstream of d0663 ORF through approximate 200 nt downstream of c09478 ORF was obtained by PCR from genomic DNA of *P. ananatis* SC17 using primers P3(SEQ ID NO: 9) and P4(SEQ ID NO: 10) with PrimeSTAR DNA polymerase (Takara Bio Inc.) (5 sec at 98° C., 10 sec at 55° C., 3 min at 72° C. for 30 cycles after 5 min at 94° C.). The obtained 2.6 kb DNA fragment was cloned into pSTV29 using BamHI sites designed at the 5' end of each primer to obtain the plasmid pSTV-PA36ccd, in which c09478 gene was oriented in the same direction as the lacZ promoter located on pSTV29.

1-3. Effect of c0011 and d0663-c09478 on Resistance to Cysteine.

To test the effect of c0011 gene and the gene locus containing two genes d0663 and c09478 on the resistance of cysteine, pSTV-c0011 PF and pSTV-PA36ccd, and the corresponding vector pSTV29 as a control were introduced in *E. coli* strain MG1655 (ATCC47076, ATCC 700926) and each transformant was grown in M9 minimal medium (Sambrook et al., Molecular cloning, 3rd edition, 2001 Cold Spring Harbor Laboratory Press) containing a toxic concentration of L-cysteine for wild-type or control strains. Each of the overnight cultures cultivated at 34° C. in a test tube containing 3 ml of M9 minimal medium supplemented with 0.4% glucose (M9Glc media) was diluted 1:100 into fresh M9Glc medium containing 50 M cysteine in a total of 3 ml and grown at 34° C. in test tubes with agitation overnight. Then the cells were inoculated to 4 ml of fresh M9Glc medium in test tubes containing 0 and 200 M of L-cysteine to give an initial $OD_{660}$ of 0.007. $OD_{660}$ nm was monitored automatically using TN-1506 incubator (Advantec Toyo, Tokyo, Japan). For maintenance of the plasmids, 25 mg/L of chloramphenicol was supplemented into the medium. The obtained growth curves are shown in FIG. 1. As can be seen in FIG. 1, the strains carrying the plasmids pSTV-c0011 PF and pSTV-PA36ccd grew faster than the control strain carrying the vector pSTV29 under 200 M cysteine conditions indicating that these gene/gene locus confer resistance to cysteine. The effects can possibly be attributed to the efflux of cysteine by c0011 and d0663 in which the toxic effects of intercellular cysteine are relieved, since their secondary structure predictions suggest that they have multiple transmembrane helixes that are typical of transporters which are able to transport small molecules across the membrane.

Example 2

Effect of c0011 on the Fermentative Production of Cysteine 2-1. Construction of a Plasmid for Over-Expression of c0011.

Two types of expression plasmids pMIV-Pnlp0 and pNIV-Pnlp23 with different promoter strength were used for the over-expression of c0011. These plasmids contain the strong nlp0 promoter (or nlp23 promoter) and the rrnB terminator so that the target genes can be cloned between these structures to form an expression unit. The promoter "Pnlp0" (SEQ ID NO: 11) was derived from the promoter of the nlpD gene of *E. coli* K-12, "Pnlp23" (SEQ ID NO: 12) and "Pnlp8" (SEQ ID NO: 13) (see below for further details) are the variants with different strengths of the promoter activity (U.S. Patent Application Publication No. 2010/209977). The overall scheme of the construct of these expression plasmids is described below (see Reference Example 1) as a construct of plasmid pMIV-Pnlp0-YeaS3 where yeaS gene from *E. coli* K-12 is cloned between nlp0 promoter and rrnB terminator using the unique restriction sites of SalI and XbaI designed at the start and end of the ORF respectively. In order to obtain pMIV-Pnlp0-based expression plasmid for c0011, the same construct with SalI and XbaI can be applied to replace the yeaS gene on the pMIV-Pnlp0-YeaS3 with c0011 gene to yield pMIV-Pnlp0-c0011. Also, pMIV-Pnlp23-c0011 can be obtained with the same schematic approach using SalI and XbaI since the basic structures of these two plasmids are mostly the same except they have a few nucleotides changes in the promoter region.

A DNA fragment containing c0011ORF was obtained by PCR from genomic DNA of *P. ananatis* SC17 using primers P5 (SEQ ID NO: 14) and P6 (SEQ ID NO: 15) with PrimeSTAR DNA polymerase (Takara Bio Inc.) (5 sec at 98° C., 5 sec at 55° C., 90 sec at 72° C. for 30 cycles after 5 min at 94° C.). The resulting DNA fragment was cloned into pMIV-Pnlp0 and pMIV-Pnlp23 using SalI and XbaI sites designed at the 5' end of each primer to obtain plasmids pMIV-Pnlp0- c0011 and pMIV-Pnlp23-c0011, respectively. The plasmid pMIV-5JS (JP2008-99668, EP1942183)) was routinely used for a corresponding empty vector as a control.

2-2. Construction of the Cysteine Producing Strains.

To prepare *E. coli* and *P. ananatis* strains which are capable of fermentative production of cysteine, a plasmid carrying cysEX gene which encodes a feedback resistant mutant of O-acetyl-L-serine sulfhydrylase (U.S. Patent Application Publication No. 2005/0112731 A1), an essential factor for the cysteine production, was constructed. For this purpose, pACYC-DE1, which carries cysEX and ydeD gene (U.S. Pat. No. 5,972,663A), was used as a start material. Construction of pACYC-DE1 is described in U.S. Patent Application Publication No. 2010/209977, as the construction of pACYC-DES (U.S. Patent Application Publication No. 2005/124049, this plasmid carries three genes cysEX, ydeD and serA5 (U.S. Pat. No. 6,180,373)), in which the cloning step of serA5 on the plasmid is omitted so that only cysEX and ydeD are placed on the plasmid. Then pACYC-DE1 was digested with restriction enzyme MluI and was subjected to self-ligation to delete the 330 bp region inside the ORF of ydeD to give pACYC-E1. Thus, the plasmid pACYC-E1 contains only cysEX, whose introduction provides the simplest cysteine producing strains. *E. coli* MG1655 and *P. ananatis* SC17 strains were transformed with pACYC-E1 to obtain the strains MG1655/pACYC-E1 and SC17/pACYC-E1, respectively, which were used as the basic producer strains for the fermentative production of cysteine.

2-3. Effect of c0011 on the Production of Cysteine in *E. Coli.*

To test the effects of c0011 over-expression on the production of cysteine, pMIV-Pnlp0-c0011, pMIV-Pnlp23-c0011, and pMIV-5JS (control) were introduced into the cysteine producing strain MG1655/pACYC-E1. The resulting strains were subjected to the production tests comparing capacity of the fermentative production of cysteine. Components of the medium for the fermentation experiments are described below.

The composition of the fermentation medium was as follows (final conc.):

| | |
|---|---|
| Component 1: | |
| $(NH_4)_2SO_4$ | 15 g/L |
| $KH_2PO_4$ | 1.5 g/L |
| $MgSO_4 \cdot 7H_2O$ | 1 g/L |
| thiamine HCl | 0.1 mg/L |
| Component 2: | |
| $FeSO_4 \cdot 7H_2O$ | 1.7 mg/L |
| $Na_2MoO_4 \cdot 2H_2O$ | 0.15 mg/L |
| $CoCl_2 \cdot 6H_2O$ | 0.7 mg/L |
| $MnCl \cdot 4H_2O$ | 1.6 mg/L |
| $ZnSO_4 \cdot 7H_2O$ | 0.3 mg/L |
| $CuSO_4 \cdot 5H_2O$ | 0.25 mg/L |
| Component 3: | |
| Bacto Tryptone | 0.6 g/L |
| Bacto Yeast Extract | 0.3 g/L |
| NaCl | 0.6 g/L |
| Component 4: | |
| $CaCO_3$ | 20 g/L |
| Component 5: | |
| L-histidine HCl $H_2O$ | 135 mg/L |
| Component 6: | |
| $Na_2S_2O_3$ | 4 g/L |

-continued

| | |
|---|---|
| Component 7: | |
| pyridoxine HCl | 2 mg/L |
| Component 8: | |
| Glucose | 40 g/L |

Each component was prepared as a concentrated stock of 10× (component 1), 1000× (component 2), 100/6× (component 3), 100× (component 5), 350/4× (component 6), 1000× (component 7) and 10× (component 8), respectively. Sterilization conditions were: autoclaving at 110° C. for 30 min (component 1, 2, 3, 5 and 8), dry heat sterilization at 180° C. for more than 5 hrs (component 4) and filter sterilization (component 6 and 7).

The fermentation was carried out as described in the following. Each producing strain (MG1655/pACYC-E1) carrying pMIV-Pnlp0-c0011, pMIV-Pnlp23-c0011, and pMIV-5JS was streaked onto LB plate and grown at 34° C. overnight. A loop-full of cells (scratched cells over 7 cm using 10 micro litter blue loop (NUNC) from the fully grown plate culture) were taken and inoculated into 2 ml of the medium for fermentation in the test tubes (23 mm internal diameter; all test tubes were 200 mm long) to initiate cultivation. The cultivation was carried out at 32° C. with agitation and then terminated when all the sugar was consumed (it took 21 to 24 hrs depending on the samples). The amount of cysteine-related compounds which were produced in the culture broth was determined routinely by the method described by Gaitonde, M. K. (Biochem J.; 104(2):627-33 (1967)). To maintain the plasmids, 25 mg/L of chloramphenicol and mg/L of tetracycline was supplemented into the medium over the course of cultivation.

The amounts of the cysteine-related compounds and yield against consumed sugar with corresponding values of standard deviation from (four independent test tube fermentation) are shown in Table 1. As can be seen from Table 1, over-expression of c0011 has positive effects on increasing the production of cysteine (including cysteine-related compounds) in *E. coli*, which is likely to be due to its capacity for efflux of cysteine.

TABLE 1

| Strain | Cysteine (mg/L) | Yield (%) |
|---|---|---|
| MG1655/pACYC-E1/pMIV-5JS | 160 ± 57 | 0.40 ± 0.14 |
| MG1655/pACYC-E1/pMIV-Pnlp23-c0011 | 737 ± 101 | 1.84 ± 0.25 |
| MG1655/pACYC-E1/pMIV-Pnlp0-c0011 | 565 ± 83 | 1.41 ± 0.21 |

2-4. Effect of c0011 on the Production of Cysteine in *P. Ananatis.*

To test the effect of c0011 over-expression on the production of cysteine in *P. ananatis*, the plasmids pMIV-Pnlp0-c0011, pMIV-Pnlp23-c0011, and pMIV-5JS (control) were introduced into the cysteine-producing strain SC17/pACYC-E1. The productive cultivation was executed as described in the experiment with *E. coli* except the cultivation time was 18 hrs. Amounts of cysteine-related compounds and yield against consumed sugar with corresponding values of standard deviation from data for each strain (four independent test tube fermentations) are shown in Table 2. As can be seen from Table 2, over-expression of c0011 has positive effects on increasing the production of cysteine in *P. ananatis*.

TABLE 2

| Strain | Cysteine (mg/L) | Yield (%) |
|---|---|---|
| SC17/pACYC-E1/pMIV-5JS | 95 ± 6 | 0.24 ± 0.018 |
| SC17/pACYC-E1/pMIV-Pnlp23-c0011 | 248 ± 71 | 0.41 ± 0.012 |
| SC17/pACYC-E1/pMIV-Pnlp0-c0011 | 209 ± 16 | 0.35 ± 0.027 |

Example 3

Effect of c0011 on the Fermentative Production of Amino Acids 3-1. Effect of c0011 on the Production of Amino Acids in *E. Coli.*

To test the effect of c0011 over-expression on the production of amino acids other than cysteine, pMIV-Pnlp0-c0011 and pMIV-5JS (control) were introduced into MG1655. Resulting strains were subjected to the production tests comparing capacity of the fermentative production of amino acids. The productive cultivation was executed as described in the experiment for cysteine production with *E. coli*, except cultivation time was 19-24.5 hrs. For maintenance of the plasmids, 25 mg/L of chloramphenicol was supplemented into the medium during the course of cultivation. Quantitative analysis of produced L-amino acids in the culture medium was performed using Amino Acid Analyzer L-8900 (HITACHI). Amounts of amino acids with corresponding values of standard deviation from data for each strain (four independent test tube fermentations) are shown in Table 3. As can be seen in Table 3, over-expression of c0011 has positive effects on increasing the production of valine, leucine, isoleucine, threonine, alanine, glutamate, histidine and glycine in *E. coli*.

TABLE 3

| Strain | Val (mg/L) | Leu (mg/L) | Ile (mg/L) | Thr (mg/L) | Glu (mg/L) | Gly (mg/L) | Ala (mg/L) | His (mg/L) |
|---|---|---|---|---|---|---|---|---|
| MG1655/pMIV-5JS | 13 ± 2.5 | 5.2 ± 1.8 | 0.4 ± 0.7 | 2.7 ± 0.9 | 891 ± 289 | 0.4 ± 0.3 | 54 ± 28 | 14 ± 2.5 |
| MG1655/pMIV-Pnlp0-c0011 | 320 ± 14 | 205 ± 41 | 65 ± 11 | 101 ± 41 | 1470 ± 15 | 6.1 ± 0.8 | 307 ± 13 | 37 ± 3.4 |

3-2. Effect of c0011 on the Production of Amino Acids in *P. Ananatis.*

To test the effect of c0011 over-expression on the production of amino acids other than cysteine, pMIV-Pnlp0-c0011 and pMIV-5JS (control) were introduced into SC 17. Resulting strains were subjected to the production tests comparing capacity of the fermentative production of amino acids. The productive cultivation was executed as described in the experiment for cysteine production with *E. coli*, except the initial glucose concentration was set to 60 g/L and cultivation time was 16 hrs. For maintenance of the plasmids, 25 mg/L of chloramphenicol was supplemented into the medium during the course of cultivation. Quantitative analysis of produced amino acids in the culture media was performed using Amino Acid Analyzer L-8900 (HITACHI). Amounts of amino acids with corresponding values of standard deviation from data for each strain (four independent test tube fermentations) are shown in Table 4. As can be seen in Table 4, over-expression of c0011 has positive effects on increasing the production of valine, leucine and isoleucine in *P. ananatis*, which is similar to the results in *E. coli* for production of all these amino acids.

TABLE 4

| Strain | Val (mg/L) | Leu (mg/L) | Ile (mg/L) |
|---|---|---|---|
| SC17/pMIV-5JS | 16 ± 7.2 | 2.7 ± 0.9 | 2.3 ± 0.3 |
| SC17/pMIV-Pnlp0-c0011 | 112 ± 7.6 | 6.8 ± 0.3 | 6.0 ± 0.2 |

Example 4

Effect of d0663 And d0663-c09478 Locus on the Fermentative Production of Cysteine 4-1. Construction of a Plasmid for Over-Expression of d0663 and d0663-c09478 Locus.

A DNA fragment containing approximate 200 nt downstream of d0663 ORF through approximate 200 nt downstream of c09478 ORF was obtained by PCR from genomic DNA of *P. ananatis* SC17 using primers P3 and P4 with PrimeSTAR DNA polymerase (Takara Bio Inc.) (5 sec at 98° C., 10 sec at 55° C., 3 min at 72° C. for 30 cycles after 5 min at 94° C.). A DNA fragment containing approximate 300 nt upstream and 200 nt downstream of the d0663 ORF was obtained by PCR from genomic DNA of *P. ananatis* SC17 using primers P3 and P7 (SEQ ID NO: 16) with PrimeSTAR DNA polymerase (Takara Bio Inc.) (5 sec at 98° C., 10 sec at 55° C., 3 min at 72° C. for 30 cycles after 5 min at 94° C.). The obtained 2.6 kb DNA fragment containing the ORFs d0663 and c09478, and a 1.1 kb fragment containing the d0663 ORF were cloned into pACYC177 (NIPPON GENE CO., LTD., Tokyo, Japan) using BamHI sites designed at the 5' end of each primer to obtain plasmids pACYC-PA36ccd and pACYC-d0663F, respectively, in which c09478 on pACYC-PA36ccd and d0663 on pACYC-d0663F, respectively, were oriented in the same direction as the Km$^r$ gene located on pACYC177.

In addition to that, pMIV-Pnlp8-based expression plasmids (see Example 2-1 and Example 4-2) for d0663 were constructed. A DNA fragment containing P8 (SEQ ID NO: 17) and P9 (SEQ ID NO: 18) with PrimeSTAR DNA polymerase (Takara Bio Inc.) (5 sec at 98° C., 5 sec at 55° C., 90 sec at 72° C. for 30 cycles after 5 min at 94° C.). Resulting DNA fragment was cloned into pMIV-Pnlp8 using SalI and XbaI sites designed at the 5' end of each primer to yield a plasmid pMIV-Pnlp8-d0663. Two variant clones from pMIV-Pnlp8-d0663 that confer a higher level of cysteine resistance to *E. coli* (see Example 1 for the resistance against cysteine) than that with the originally constructed pMIV-Pnlp8-d0663 were obtained during a course of experiments. According to the sequencing analysis of the plasmids, mutations were located not on the d0663 ORF itself but a few nucleotides upstream from the initiation codon of d0663 raising the possibility of a translational change providing elevated expression level. The exact location and base substitution of the one mutant was C(−3)G (3$^{rd}$ nucleotide upstream from start codon "G" was substituted by "C") and the other was C(−4)A; these variant plasmids were named pMIV-Pnlp8-d0663(−3) and pMIV-Pnlp8-d0663(−4) respectively and used as highly active expression plasmids of d0663. These mutants can be constructed with well-known site-directed mutagenesis using pMIV-Pnlp8-d0663 as a start material as well. The plasmid pMIV-5JS (JP2008-99668) was routinely used for a corresponding empty vector as a control.

4-2. Construction of the Cysteine Producing Strains.

MG1655/pACYC-E1 described in Example 2-2 was used as an *E. coli* strain capable of fermentative production of cysteine.

For *P. ananatis* cysteine-producing strains, SC17/pMIV-CysE5 and EYPSGint1M2 were prepared. Overall schematic procedures for the construction are described below.

The plasmid pMIV-CysE5 provides a feedback resistant mutant allele of O-acetyl-L-serine sulfhydrylase (US20050112731A1) encoded by cysE5, an essential factor for the cysteine production. A DNA fragment containing the cysE5 allele was obtained by PCR from pMW-PompC-cysE5 (EP1650296A1) as a template using primers P10 (SEQ ID NO: 19) and P11 (SEQ ID NO: 20) (30 sec at 94° C., 30 sec at 57° C., 1 min at 72° C. for 27 cycles and then held at 72° C. for 7 min). The obtained 0.7 kb DNA fragment containing cysE5 was cloned into pMIV-PompC using SalI and XbaI sites designed at the 5' end of each primer to yield pMIV-CysE5. The plasmid pMIV-PompC was constructed by cloning the 0.3 kb fragment containing the promoter region of ompC gene from *E. coli* K-12 into pMIV-5JS (JP2008-99668) using SalI and PaeI, where the fragment was obtained by PCR from genomic DNA of *E. coli* MG1655 using primers P12 (SEQ ID NO: 21) and P13 (SEQ ID NO: 22) and digested by SalI and PaeI prior to ligation. pMIV-CysE5 was introduced into *P. ananatis* SC17 to provide the cysteine-producing strain SC17/pMIV-CysE5.

Construction of Strain EYPSGint1M2, is Described in the Reference Example 1.

4-3. Effect of d0663 on the Production of Cysteine in *E. Coli.*

To test the effect of d0663 over-expression on the production of cysteine, pMIV-Pnlp8-d0663(−3), pMIV-Pnlp8-d0663(−4) and pMIV-5JS (control) were introduced into the cysteine producing strain MG1655/pACYC-E1. Resulting strains were subjected to the production tests comparing capacity of the fermentative production of cysteine. The productive cultivation was executed as described in the experiment with c0011 in *E. coli* (see Example 2-3) except the cultivation time was 19 hrs. For maintenance of the plasmids, 25 mg/L of chloramphenicol and 20 mg/L of tetracycline were supplemented during the course of cultivation. The amount of cysteine-related compounds and yield against consumed sugar with corresponding values of standard deviation from data for each strain (four independent test tube fermentations) are shown in Table 5. As can be seen in Table 5, over-expression of d0663 has positive effects on increasing the production of cysteine in *E. coli*.

TABLE 5

| Strain | Cysteine (mg/L) | Yield (%) |
|---|---|---|
| MG1655/pACYC-E1/pMIV-5JS | 246 ± 21 | 0.7 ± 0.07 |
| MG1655/pACYC-E1/pMIV-Pnlp8-d0663(-3) | 949 ± 78 | 2.5 ± 0.20 |
| MG1655/pACYC-E1/pMIV-Pnlp8-d0663(-4) | 980 ± 110 | 2.6 ± 0.23 |

4-4. Effect of d0663 and d0663-c09478 Locus on the Production of Cysteine in *P. Ananatis.*

To determine the effects of d0663 and d0663-c09478 locus over-expression on the production of cysteine, pACYC-d0663F, pACYC-PA36ccd (contains two ORFs, d0663 and c09478) and pACYC177 (control) were introduced into the cysteine-producing strain SC17/pMIV-CysE5. Resulting strains were subjected to the production tests comparing capacity of the fermentative production of cysteine. The productive cultivation was executed as described in the experiment for cysteine production with c0011 in *E. coli* (see Example 2-3) except initial glucose concentration was set to 60 g/L and cultivation time was 16-20 hrs. For maintenance of the plasmids, 25 mg/L of chloramphenicol and 20 mg/L of kanamycin was supplemented into the medium during the course of cultivation. The amount of cysteine-related compounds and yield against consumed sugar with corresponding values of standard deviation from data for each strain (four independent test tube fermentations) are shown in Table 6. As can be seen in Table 6, over-expression of d0663 has positive effects on increasing the production of cysteine in *P. ananatis*. It was found that addition of c09478 accelerated the effects of d0663 as pACYC-PA36ccd doubled the production of cysteine as compared to the production with pACYC-d0663F.

TABLE 6

| Strain | Cysteine (mg/L) | Yield (%) |
|---|---|---|
| SC17/pMIV-CysE5/pACYC177 | 200 ± 62 | 0.3 ± 0.10 |
| SC17/pMIV-CysE5/pACYC-d0663F | 496 ± 75 | 0.8 ± 0.13 |
| SC17/pMIV-CysE5/pACYC-PA36ccd | 906 ± 96 | 1.5 ± 0.16 |

Same experiments were performed using EYPSGint1M2 as a cysteine-producer strain. Again, the plasmids pACYC-d0663F, pACYC-PA36ccd (contains two ORFs, d0663 and c09478) and pACYC177 (control) were introduced, and the resulting strains were subjected to the production tests described in the experiment for cysteine production with c0011 in *E. coli* (see Example 2-3). For maintenance of the plasmids, 20 mg/L of kanamycin was supplemented during the course of cultivation. The amount of cysteine-related compounds and yield against consumed sugar with corresponding values of standard deviation from data for each strain (four independent test tube fermentations) was shown in Table 7. As can be seen in Table 7, over-expression of d0663 has positive effects on increasing the production of cysteine in *P. ananatis*, which was further promoted by the addition of c09478.

TABLE 7

| Strain | Cysteine (g/L) | Yield (%) |
|---|---|---|
| EYPSGint1M2/pACYC177 | 0.55 ± 0.10 | 1.4 ± 0.24 |
| EYPSGint1M2/pACYC-d0663F | 0.96 ± 0.15 | 2.4 ± 0.37 |
| EYPSGint1M2/pACYC-PA36ccd | 1.34 ± 0.20 | 3.4 ± 0.49 |

Example 5

Effects of d0663 on the Fermentative Production of Amino Acids 5-1. Effect of d0663 on the Production of Amino Acids in *P. Ananatis.*

To determine the effects of d0663 over-expression on the production of amino acids, pMIV-Pnlp8-d0663(−3), pMIV-Pnlp8-d0663(−4) and pMIV-5JS (control) were introduced into *P. ananatis* SC17. Resulting strains were subjected to the production tests comparing capacity of the fermentative production of amino acids. The productive cultivation was executed as described in the experiment for cysteine production with c0011 in *E. coli* (see Example 2-3) except the initial glucose concentration was set to 60 g/L and cultivation time was 18 hrs. For maintenance of the plasmids, 25 mg/L of chloramphenicol was supplemented during the course of cultivation. Quantitative analysis of produced amino acids in the culture media was performed using Amino Acid Analyzer L-8900 (HITACHI). Amount of amino acids with corresponding values of standard deviation from data for each strain (four independent test tube fermentation) are shown in Table 8. As can be seen in Table 8, over-expression of d0663 has positive effects on increasing the production of valine, leucine, isoleucine and threonine.

TABLE 8

| Strain | Val (mg/L) | Leu (mg/L) | Ile (mg/L) | Thr (mg/L) |
|---|---|---|---|---|
| SC17/pMIV-5JS | 105.6 ± 9.3 | 5.8 ± .5 | 3.7 ± 0.3 | 2.1 ± 0.1 |
| SC17/pMIV-Pnlp8-d0663(-3) | 1286.2 ± 21.0 | 111.7 ± 6.9 | 61.8 ± 3.5 | 58.4 ± 0.1 |
| SC17/pMIV-Pnlp8-d0663(-4) | 1367.1 ± 27.1 | 134.0 ± 5.8 | 67.1 ± 2.7 | 62.2 ± 3.4 |

Example 6

Effect of Putative Cys Exporters on the Fermentative Production of L-Valine by *E. Coli*

6-1. Effect of d0663(−4) on the Production of L-Valine in *E. Coli*

To test effect of d0663(−4) over-expression on the production of valine, pMIV-Pnlp8-d0663 (−4) and pMIV-5JS (control) plasmids were introduced into the L-valine producing strain H-81. The strain H-81 has been deposited in the Russian National Collection of Industrial Microorganisms (VKPM) (Russia 113545, Moscow, 1 Dorozhny proezd, 1) on Jan. 30, 2001 under accession number VKPM B-8066, and converted to an international deposit based on Budapest Treaty on Feb. 1, 2002. Resulting strains were subjected to the production tests comparing capacity of the fermentative production of L-valine. Cells from stock tube (stored in % glycerol, 0.9% NaCl at −70° C.) were plated on L-agar (yeast extract—5 g/l, peptone—10 g/l, NaCl—5 g/l, agar—15 g/l). For plasmid strains L-agar was supplemented with appropriate antibiotic (Ap—100 mg/l, Km—40 mg/l). Cells from about 0.5 $cm^2$ of plate surface were inoculated into fermentation medium (2 ml) and cultivated for 72 hours at 32° C. The composition of the fermentation medium was as follows: sucrose—60 g/l, $(NH_4)_2SO_4$—15 g/l, $KH_2PO_4$—1.5 g/l, $MgSO_4$—1 g/l, thiamin—0.1 g/l, Mameno (TN)—0.4 g/l, $CaCO_3$—25 g/l, pH 7.0 (KOH), appropriate antibiotics (Km, 50 mg/l; Ap, 100 mg/l) were added into the medium.

Quantitative analysis of produced valine in the culture medium was performed using Amino Acid Analyzer L-8900 (HITACHI). Amount of valine with corresponding values of standard deviation from data for each strain (four independent test tube fermentations) are shown in Table 9. As can be seen in Table 9, over-expression of d0663(−4) have positive effects on increasing the production of L-valine by *E. coli*.

TABLE 9

| Strain | Val (g/L) | $OD_{540}$ |
|---|---|---|
| H-81/pMIV-5JS | 11.2 ± 0.3 | 33.2 ± 1.2 |
| H-81/pMIV-Pnlp8-d0663(-4) | 13.2 ± 1.2 | 28.7 ± 1.2 |

6-2. Effect of c0011 on the Production of L-Valine in *E. Coli*

To test effect of c0011 overexpression on the production of L-valine, the pMIV-Pnlp23-c0011 plasmid was introduced into the valine-producing strain H-81. Resulting strain together with parent H-81 strain was subjected to the production tests comparing capacity of the fermentative production of L-valine using fed-batch cultivation in Marubishi fermentors.

Cells were plated on L-agar (yeast extract—5 g/l, peptone-10 g/l, NaCl—5 g/l, agar—15 g/l). For plasmid strain, L-agar was supplemented with appropriate antibiotic (Ap—100 mg/l, Km—40 mg/l). Cells from about 0.5 $cm^2$ of plate surface were inoculated into L-broth (tryptone—10 g/l, yeast extract—5 g/l, NaCl—5 g/l) medium (60 ml) and cultivated for 20 hours at 37° C. at 240 rpm. Then 40 ml of seed culture were transferred to 360 ml of fermentation medium in jar-fermentor and cultivated for 20 hours at 37° C. initially with agitation at 1200 rpm and after 18 hours of cultivation at 900 rpm.

The composition of the fermentation medium was as follows: glucose—30 g/l, $MgSO_47H_2O$—0.4 g/l, Mameno (TN)—0.4 g/l, $(NH_4)_2SO_4$—5.0 g/l, $KH_2PO_4$—3.0 g/l, $FeSO_47H_2O$—0.02 g/l, $MnSO_45H_2O$—0.02 g/l, thiamin—0.4 mg/l, antifoam—0.1 mg/l, pH 6.6 (KOH). Mixed feed (glucose—140 g, $H_2O$-100 ml, concentrate aqueous ammonia—53 ml) was added automatically to maintain a constant pH of 6.6.

The data on production of valine are presented in Table 10. As can be seen in Table 10, over-expression of c0011 has positive effect on increasing the production of valine in *E. coli*.

TABLE 10

| Strain | Y, % | OD | Val g/l | Val g/l h |
|---|---|---|---|---|
| H-81 | 24.3 | 133 | 41.1 | 2.0 |
| H-81/pMIV-Pnlp23-c0011 | 26.3 | 98 | 50.6 | 2.5 |

Example 7

Effects of d0663 on the Production of O-Acetyl-L-Serine in *E. Coli*

To determine effects of d0663 over-expression on the production of O-acetyl-L-serine, pMIV-Pnlp8-d0663(−3) and pMIV-5JS (control) plasmids were introduced into the cysteine-producing strain MG1655/pACYC-E1. Since the strain MG1655/pACYC-E1 carries feed-back resistant CysE mutant on the plasmid, this strain is suitable for producing O-acetyl-L-serine. Resulting strains were subjected to the production tests comparing capacity of the fermentative production of O-acetyl-L-serine. The productive cultivation was executed as described in the experiment with c0011 in *E. coli* (see Example 2) except cultivation time was 26 hours. For maintenance of the plasmids, 25 mg/L of chloramphenicol and 12.5 mg/L of tetracycline were supplemented during the course of cultivation. In order to convert produced O-acetyl-L-serine to N-acetylserine (NAS) at alkaline pH, samples were diluted using 200 mM Tris/HCl (pH9.0). Resulting NAS was analyzed using HPLC. The analytic conditions for HPLC were the following: column: Inertsil ODS-3 (GL science), flow rate: 1.0 ml/min, column temperature: 40° C., detector: UV210 mm, sample volume: 10:1, buffer: 0.1M $K_2PO_4$—$H_3PO_4$ (pH2.2) 5 mM sodium 1-octanesulfonate. Amount of O-acetyl-L-serine and yield against consumed sugar with corresponding values of standard deviation from triplicate data for each strain was shown in Table 11. The obtained data suggests that over-expression of d0663 has positive effects on increasing the production of O-acetyl-L-serine in *E. coli*.

TABLE 11

| Strain | O-acetyl-L-serine (g/L) | Yield (%) |
|---|---|---|
| MG1655/pACYC-E1/pMIV-5JS | 0.20 ± 0.20 | 0.60 ± 0.51 |
| MG1655/pACYC-E1/pMIV-Pnlp8-d0663(-3) | 4.1 ± 0.34 | 10.3 ± 0.86 |

Example 8

Effects of c0011 on the Production of O-Acetyl-L-Serine in *E. Coli*

To determine effects of c0011 over-expression on the production of O-acetyl-L-serine, pMIV-Pnlp23-c0011 and pMIV-5JS (control) plasmids were introduced into the cysteine/O-acetyl-L-serine producing strain MG1655/pACYC-E1. All the productive cultivation and analytic procedures were the same as described in the production of O-acetyl-L-serine with d0663 enhanced strain (see example 7). Amount of produced O-acetyl-L-serine and yield against consumed sugar with corresponding values of standard deviation from triplicate data for each strain was shown in Table 12. The obtained data suggests that over-expression of c0011 has positive effects on increasing the production of O-acetyl-L-serine in *E. coli*.

TABLE 12

| Strain | O-acetyl-L-serine (g/L) | Yield (%) |
|---|---|---|
| MG1655/pACYC-E1/pMIV-5JS | 0.60 ± 0.04 | 1.49 ± 0.11 |
| MG1655/pACYC-E1/pMIV-Pnlp23-c0011 | 2.46 ± 0.86 | 6.16 ± 2.15 |

Reference Example 1

Construction of a Strain with Enhanced Expression of the Gene cysM

1. Construction of the Strain *P. Ananatis* EYPS1976(s)

The DNA fragment containing promoter of the gene nlpD from *E. coli* was obtained using PCR. The chromosomal DNA of *E. coli* MG1655(ATCC 700926) strain as a template and primers P14 (SEQ ID No:23) and P15 (SEQ ID No:24) were used for PCR. Primer P14 (SEQ ID No:23) contains a site for SalI restrictase at the 5'-end thereof. Primer P15 (SEQ ID No:24) contains a site for PaeI restrictase at the 5'-end thereof. Conditions for PCR were as follows: denaturation step for 3 min at 95° C.; profile for two first cycles: 1 min at 95° C., 30 sec at 50° C., 40 sec at 72° C.; profile for the last 25 cycles: 20 sec at 94° C., 20 sec at 55° C., 15 sec at 72° C.; final step: 5 min at 72° C. The amplified DNA fragment was about 0.2 kb in size, it was purified by agarose gel electrophoresis. Then, the purified fragment was treated with endonucleases PaeI and SalI. The obtained DNA fragment was then ligated with plasmid pMIV-5JS (construction of the plasmid pMIV-5JS is described in EP1942183B1) previously treated with endonucleases PaeI and SalI. The mixture for ligation was incubated at 4° C. overnight and was then used to transform *E. coli* strain MG1655 by electroporation. The transformants were plated on plates with LB agar containing ampicillin (50 mg/l), the plates were incubated at 37° C. overnight until individual colonies became visible. Plasmids were isolated from obtained transformants and analyzed by restriction analysis. The obtained plasmid containing the promoter of the gene nlpD from *E. coli* was named pMIV-Pnlp0.

The DNA fragment containing terminator of the gene rrnB from *E. coli* was obtained using PCR. The chromosomal DNA of *E. coli* MG1655 strain as a template and primers P16 (SEQ ID No:25) and P17 (SEQ ID No:26) were used for PCR. Primer P16 (SEQ ID No:25) contains a site for XbaI restrictase at the 5'-end thereof. Primer P17 (SEQ ID No:26) contains a site for BamHI restrictase at the 5'-end thereof. Conditions for PCR were as follows: denaturation step for 3 min at 95° C.; profile for two first cycles: 1 min at 95° C., 30 sec at 50° C., sec at 72° C.; profile for the last 25 cycles: 20 sec at 94° C., 20 sec at 59° C., 15 sec at 72° C.; final step: 5 min at 72° C. The amplified DNA fragment was about 0.3 kb in size, and it was purified by agarose gel electrophoresis. Then, the purified fragment was treated with endonucleases BamHI and XbaI. The obtained DNA fragment was then ligated with plasmid pMIV-Pnlp0 previously treated with endonucleases BamHI and XbaI. The mixture for ligation was incubated at 4° C. overnight and was then used to transform *E. coli* strain MG1655 by electroporation. The transformants were plated on plates with LB agar containing ampicillin (50 mg/l), the plates were incubated at 37° C. overnight until individual colonies became visible. Plasmids were isolated from obtained transformants and analyzed by restriction analysis. The obtained plasmid containing the terminator of the gene rrnB from *E. coli* was named pMIV-Pnlp0-ter.

The DNA fragment containing the gene yeaS from *E. coli* was obtained using PCR. The chromosomal DNA of *E. coli* MG1655 strain as a template and primers P18 (SEQ ID No:27) and P19 (SEQ ID No:28) were used for PCR. Primer P18 (SEQ ID No:27) contains a site for SalI restrictase at the 5'-end thereof. Primer P19 (SEQ ID No:28) contains a site for XbaI restrictase at the 5'-end thereof. Conditions for PCR were as follows: denaturation step for 3 min at 95° C.; profile for two first cycles: 1 min at 95° C., 30 sec at 50° C., 40 sec at 72° C.; profile for the last 25 cycles: 20 sec at 94° C., 20 sec at 55° C., 15 sec at 72° C.; final step: 5 min at 72° C. The amplified DNA fragment was about 0.7 kb in size, and it was purified by agarose gel electrophoresis. Then, the purified fragment was treated with endonucleases SalI and XbaI. The obtained DNA fragment was then ligated with plasmid pMIV-Pnlp0-ter previously treated with endonucleases SalI and XbaI. The mixture for ligation was incubated at 4° C. overnight and was then used to transform *E. coli* strain MG1655 by electroporation. The transformants were plated on plates with LB agar containing ampicillin (50 mg/l), the plates were incubated at 37° C. overnight until individual colonies became visible. Plasmids were isolated from obtained transformants and analyzed by restriction analysis. The obtained plasmid containing the gene yeaS from *E. coli* was named pMIV-Pnlp0-yeaS3.

Then randomization of −10 region of promoter Pnlp and selection of the Pnlp8 promoter was performed. The 3'-end of promoter Pnlp was obtained using PCR amplification. The plasmid pMIV-Pnlp0 as a template and primers P14 (SEQ ID No:23) and P20 (SEQ ID No:29) were used for PCR. Primer P20 has random nucleotides, depicted in SEQ ID NO: 29 by the letter "n" (for A or G or C or T) and site for BglII restrictase at the 5'-end thereof. Conditions for PCR were as follows: denaturation step for 3 min at 95° C.; profile for two first cycles: 1 min at 95° C., 30 sec at 50° C., 40 sec at 72° C.; profile for the last 25 cycles: 20 sec at 94° C., 20 sec at 60° C., 15 sec at 72° C.; final step: 5 min at 72° C. 5'-end of promoter Pnlp was obtained using PCR amplification. The plasmid pMIV-Pnlp0 as a template and primers P15 (SEQ ID No:24) and P21 (SEQ ID No:30) were used for PCR. Primer P21 has random nucleotides, depicted in SEQ ID NO: 30 by the letter "n" (for A or G or C or T) and site for BglII restrictase at the 5'-end thereof. Conditions for PCR were as follows: denaturation step for 3 min at 95° C.; profile for two first cycles: 1 min at 95° C., 30 sec at 50° C., 40 sec at 72° C.; profile for the last 25 cycles: 20 sec at 94° C., 20 sec at 60° C., 15 sec at 72° C.; final step: 5 min at 72° C. Both amplified DNA fragments were purified by agarose gel electrophoresis. Then, the obtained DNA fragments were treated with endonuclease BglII followed by ligation of the fragments in equimolar proportion. The mixture for ligation was incubated at 4° C. overnight and was then used as a template for next PCR procedure, primers P14 (SEQ ID No:23) and P15 (SEQ ID No:24) were used for the PCR. Conditions for PCR were as follows: denaturation step for 3 min at 95° C.; profile for two first cycles: 1 min at 95° C., 30 sec at 50° C., 40 sec at 72° C.; profile for the last 12 cycles: 20 sec at 94° C., 20 sec at 60° C., 15 sec at 72° C.; final step: 5 min at 72° C.

The amplified DNA fragment was about 0.2 kb in size, and it was purified by agarose gel electrophoresis. Then, the purified fragment was treated with endonucleases PaeI and SalI. The obtained DNA fragment was then ligated with plasmid pMIV-Pnlp0-yeaS3 previously treated with endonucleases PaeI and SalI. The mixture for ligation was incubated at 4° C. overnight and was then used to transform *E. coli* strain MG1655 by electroporation. The transformants were plated on plates with LB agar containing ampicillin (50 mg/l), the plates were incubated at 37° C. overnight until individual colonies became visible. Plasmids were isolated from the obtained transformants and analyzed by sequencing analysis. The obtained plasmid containing promoter Pnlp8 was named pMIV-Pnlp8-yeaS7.

Then, the plasmid pMIV-Pnlp8-yeaS7 was treated with endonuclease HindIII followed by purification and treatment with DNA polymerase I large fragment (Klenow fragment). The obtained DNA fragment was purified and treated with endonuclease NcoI.

The obtained DNA fragment after purification was then ligated in equimolar proportion with plasmid pMT-Pomp-cysE5 (pMT-Pomp-cysE5 was derived from pMIV-Pomp-cysE5 by cloning of XbaI-Eco88I/Klenow fragment from pACYC-184 (tet-R) into PvuI site of pMIV-Pomp-cysE5. pMIV-Pomp-cysE5 was obtained by subcloning PaeI+SacI fragment from pMW-Pomp-cysE5 (WO2005007841) into the same sites of pMIV-5JS) previously treated with endonucleases SmaI and NcoI. The mixture for ligation was incubated at 4° C. overnight and was then used to transform *E. coli* strain MG1655 by electroporation. The transformants were plated on plates with LB agar containing ampicillin (50 mg/l), the plates were incubated at 37° C. overnight until individual colonies became visible. Plasmids were isolated from obtained transformants and analyzed by restriction analysis. The obtained plasmid containing cysE5 was named pMT-EY2. Enzymatic activity of serine acetyltransferase was measured in obtained transformant in order to confirm intactness of cysE5 allele.

The next step was to integrate cysE5 and yeaS genes into the chromosome of *P. ananatis* strain SC17 (U.S. Pat. No. 6,596,517). Plasmid pMH10 (Zimenkov D. et al., Biotechnology (in Russian), 6, 1-22 (2004)) was used to transform *P. ananatis* strain SC17 by electroporation. The transformants were plated on plates with LB agar containing kanamycin (20 mg/l), the plates were incubated at 30° C. overnight until individual colonies became visible. The obtained strain SC17/pMH10 was reseeded two times. After that, plasmid pMT-EY2 was used to transform *P. ananatis* strain SC17/pMH10 (this strain was grown at 30° C.) by electroporation. The transformants were shocked by incubation at high temperature (42° C., 20 min) and plated on plates with LB agar containing chloramphenicol (20 mg/l); the plates were incubated at 39° C. overnight until individual colonies became visible. About 50 clones were reseeded at 39° C. and each of them were inoculated in 1 ml of LA medium and incubated at 39° C. for 48 h. After incubation all 50 variants were tested for curing of the plasmids pMH10 and pMT-EY2, variants were selected which were resistant to chloramphenicol (20 mg/l) but sensitive to kanamycin (20 mg/l) and ampicillin (50 mg/l). Desired integrants were identified by PCR analysis using primers P1 and P6. The obtained line of strains was named as EY01-EY50 and all of them were tested for their ability to produce cysteine in test-tube fermentation. The best producer strain EY19 was selected and used in the following experiments.

To cure the *P. ananatis* strain EY19 from resistance to chloramphenicol, strain EY19 was transformed with the plasmid pMT-Int-Xis2 (WO2005/010175) using electroporation. The transformants were plated on plates with LB agar containing tetracycline (10 mg/l); the plates were incubated at 30° C. overnight until individual colonies became visible. The objective transformants were identified by selecting variants which were sensitive to chloramphenicol (20 mg/l). The "cured" strain was named EY19(s).

The next step was to substitute the promoter region of cysPTWA genes with the Pnlp8 promoter region in the strain EY19(s). PCR was carried out using the plasmid pMIV-Pnlp8-yeaS7 as a template and primers P14 and P15. Conditions for PCR were as follows: denaturation step for 3 min at 95° C.; profile for two first cycles: 1 min at 95° C., 30 sec at 50° C., sec at 72° C.; profile for the last 20 cycles: 20 sec at 94° C., 20 sec at 59° C., 15 sec at 72° C.; final step: 5 min at 72° C. The amplified DNA fragment was about 0.2 kb in size, and it was purified by agarose gel electrophoresis. Then, the purified fragment was treated with Klenow fragment. The DNA fragment was then ligated in equimolar proportion with plasmid pMW118-(XattL-$Km^r$-λattR) (EP2100957A1) previously treated with endonuclease XbaI followed by treatment with Klenow fragment. The mixture for ligation was incubated at 4° C. overnight and was then used to transform *E. coli* strain MG1655 by electroporation. The transformants were plated on plates with LB agar containing kanamycin (20 mg/l), the plates were incubated at 37° C. overnight until individual colonies became visible. Plasmids were isolated from the transformants and analyzed by restriction analysis. The obtained plasmid containing the Pnlp promoter was named pMW-Km-Pnlp8. Then, PCR was carried out using the plasmid pMW-Km-Pnlp8 as a template and primers P22 (SEQ ID No:31) and P23 (SEQ ID No:32). Conditions for PCR were as follows: denaturation step for 3 min at 95° C.; profile for two first cycles: 1 min at 95° C., 30 sec at 50° C., sec at 72° C.; profile for the last 30 cycles: 20 sec at 94° C., 20 sec at 54° C., 90 sec at 72° C.; final step: 5 min at 72° C. The obtained DNA fragment was about 1.6 kb in size, and it was purified by agarose gel electrophoresis and used to transform *P. ananatis* strain SC17(0) by electroporation. The transformants were plated on plates with LB agar containing kanamycin (20 mg/l); the plates were incubated at 34° C. overnight until individual colonies became visible. The objective transformants were identified by PCR analysis using primers P24 (SEQ ID No:33) and P25 (SEQ ID No:34). The obtained strain was named SC17-Pnlp8-PTWA. Chromosomal DNA was isolated from the strain SC17-Pnlp8-PTWA. 10 g of this chromosomal DNA was used to transform *P. ananatis* strain EY19(s) by electroporation. The transformants were plated on plates with LB agar containing kanamycin (20 mg/l), the plates were incubated at 34° C. overnight until individual colonies became visible. The transformants were identified by PCR analysis using primers P24 and P25. The obtained strain was named EYP197. To cure the *P. ananatis* strain EYP197 from resistance to kanamycin strain, EYP197 was transformed with the plasmid pMT-Int-Xis2 by electroporation. The transformants were plated on plates with LB agar containing tetracycline (10 mg/l); the plates were incubated at 30° C. overnight until individual colonies became visible. The objective transformants were identified by selecting variants which were sensitive to kanamycin (20 mg/l). The "cured" strain was named EY197(s).

Mutation N348A was introduced by site-specific mutagenesis. For this purpose, the 3'-end of gene serA (with mutation) was obtained by PCR amplification using chromosomal DNA of the strain SC17 as a template and primers P26 (SEQ ID No:35) and P27 (SEQ ID No:36), and the 5'-end of serA gene was obtained by PCR amplification using the chromosomal DNA of the strain SC17 as a template and primers P28 (SEQ ID No:37) and P29 (SEQ ID No:38). Both primer P27 (SEQ ID No:36) and P29 (SEQ ID No:38) contain a site for SmaI restrictase at the 5'-end thereof. Conditions for the first PCR were as follows: denaturation step for 3 min at 95° C.; profile for two first cycles: 1 min at 95° C., 30 sec at 50° C., 40 sec at 72° C.; profile for the last 25 cycles: 20 sec at 94° C., 20 sec at 60° C., 60 sec at 72° C.; final step: 5 min at 72° C. Conditions for the second PCR were as follows: denaturation step for 3 min at 95° C.; profile for two first cycles: 1 min at 95° C., 30 sec at 50° C., 40 sec at 72° C.; profile for the last 20 cycles: 20 sec at 94° C., 20 sec at 60° C., 20 sec at 72° C.; final step: 5 min at 72° C. Both amplified DNA fragments were purified by agarose gel electrophoresis followed by treatment with endonuclease SmaI. The obtained DNA fragments were then ligated in equimolar proportion. The mixture for ligation was incubated at 4° C. overnight and was used as a template for the next PCR procedure (with primers P26 and P28). Primer P26 (SEQ ID No:35) contains a site for SalI restrictase at the 5'-end thereof. Primer P28 (SEQ ID No:37) contains a site for XbaI restrictase at the 5'-end thereof. Conditions for PCR were as follows: denaturation step for 3 min at 95° C.; profile for two first cycles: 1 min at 95° C., 30 sec at 50° C., 40 sec at 72° C.; profile for the last 15 cycles: 20 sec at 94° C., 20 sec at 60° C., 75 sec at 72° C.; final step: 5 min at 72° C. The amplified DNA fragment was about 1.3 kb in size, and it was purified by agarose gel electrophoresis. The obtained fragment was treated with endonucleases SalI and XbaI. After restriction DNA fragment was ligated in equimolar proportion with the plasmid pMIV-Pnlp8-ter previously treated with endonucleases SalI and XbaI. The mixture for ligation was incubated at 4° C. overnight and was then used to transform *E. coli* strain MG1655 by electroporation. The transformants were plated on plates with LB agar containing ampicillin (50 mg/l), the plates were incubated at 37° C. overnight until individual colonies became visible. Plasmids were isolated from the transformants and analyzed by sequencing analysis. The obtained plasmid containing serA gene with mutation N348A was named pMIV-Pnlp8-serA348.

The next step was to integrate serA348 allele into chromosome of the *P. ananatis* strain SC17. Plasmid DNA pMIV-Pnlp8-serA348 was used to transform *P. ananatis* strain SC17/pMH10 (this strain was grown at 30° C.) by electroporation. The transformants were shocked by incubation at high temperature (42° C., 20 min) and plated on plates with LB agar containing chloramphenicol (20 mg/l), the plates were incubated at 39° C. overnight until individual colonies became visible. About 50 clones were reseeded at 39° C. and then each of them were inoculated in 1 ml of LA medium and incubated at 39° C. for 48 h. After incubation all 50 variants were tested for curing of the plasmids pMH10 and pMIV-Pnlp8-serA348 by selecting variants which were resistant to chloramphenicol (20 mg/l) but sensitive to kanamycin (20 mg/l) and ampicillin (50 mg/l). The objective integrants were identified by PCR analysis using primers P14 and P28. In all the obtained variants, the specific activity of PGD was measured and the most active one was selected for the following purpose. It was named SC17int-serA348.

The next step was to transfer an integrated copy of serA348 into the strain EYP197(s).

Chromosome DNA was isolated from the strain SC17int-serA348.10 g of this chromosomal DNA was used to transform *P. ananatis* EYP197(s) by electroporation. The transformants were plated on plates with LB agar containing chloramphenicol (20 mg/l), the plates were incubated at 34° C. overnight until individual colonies became visible. The objective transformants were identified by PCR analysis using primers P14 and P28. This strain was named EYPS1976.

To cure the *P. ananatis* strain EYPS1976 from resistance to chloramphenicol, strain EYPS1976 was transformed with the plasmid pMT-Int-Xis2 by electroporation. The transformants were plated on plates with LB agar containing tetracycline (10 mg/l), and the plates were incubated at 30° C. overnight until individual colonies became visible. The objective transformants were identified by selecting variants which were sensitive to chloramphenicol (20 mg/l). This "cured" strain was named EYPS1976(s).

2. Construction of the Strain EYPSGint1M2

The strain EYPSGint1M2 was obtained by integration of the cysM gene encoding O-acetylserine (thiol)-lyase B from *E. coli* into chromosome of EYPS1976(s). At the first step, integration of cysM was obtained as a result of mini-μ integration of the plasmid pMIV-Pnlp1-cysM (Reference example 2) into the chromosome of the strain SC17 using μ-transposase carrying plasmid pMH10 (as described above). The obtained construction (int(Pnlp1-cysM)) was transferred from the strain SC17 into the strain EYPS1976(s) by a chromosome transformation procedure using $Cm^R$ marker for selection. This strain was named as EYPSGint1M2 and after curing from antibiotic resistance marker, it was used for further experiments.

Reference Example 2

Construction of the Plasmid pMIV-Pnlp1-cysM

The promoter region of the gene nlpD from *P. ananatis* was amplified by PCR using primers P30 (SEQ ID NO: 39) and P31 (SEQ ID NO: 40) and chromosomal DNA of the strain SC17 as a template. The obtained DNA fragment was about 0.2 kb in size, and it was purified by agarose gel electrophoresis and digested with PaeI and SalI endonucleases followed by ligation with plasmid pMIV-5JS, previously treated with the same endonucleases.

The region of the terminator of the *E. coli* gene rrnB was amplified by PCR using primers P32 (SEQ ID NO: 41) and P33 (SEQ ID NO: 42) and chromosomal DNA of the strain MG1655 as a template. The obtained DNA fragment was about 0.25 kb in size, and it was purified by agarose gel electrophoresis and digested with XbaI and BamHI endonucleases followed by ligation with obtained at the previous step plasmid, previously treated with the same endonucleases.

The *E. coli* gene cysM was amplified by PCR using primers P34 (SEQ ID NO: 43) and P35 (SEQ ID NO: 44) and chromosomal DNA of the strain MG1655 as a template. The obtained DNA fragment was about 1.1 kb in size, and it was purified by agarose gel electrophoresis and digested with SalI and XbaI endonucleases followed by ligation with the plasmid obtained at the previous step, previously treated with the same endonucleases. Thus, the plasmid pMIV-Pnlp1-cysM was obtained.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing an L-amino acid comprising:

A) cultivating an Enterobacteriaceae bacterium that is able to produce an L-amino acid in a culture medium, and B) collecting the L-amino acid from the culture medium or the bacterium, wherein the bacterium has been modified to increase an activity of a protein which is able to confer to the bacterium resistance to growth inhibition by L-cysteine as compared to a non-modified bacterium, wherein said protein is selected from the group consisting of:

(a) the protein of SEQ ID NO: 4 and (b) a protein having at least 95% sequence identity to the entire amino acid sequence of SEQ ID NO: 4.

2. The method according to claim 1, wherein expression of a DNA encoding said protein in said bacterium is enhanced as compared to a non-modified bacterium.

3. The method according to claim 1, wherein said bacterium is transformed with a DNA encoding said protein.

4. The method according to claim 2, wherein the DNA comprises a d0663 gene having the sequence of SEQ ID NO: 3.

5. The method according to claim 1, wherein said bacterium has been further modified to express a DNA encoding the protein of SEQ ID NO: 6 or a protein having at least 95% sequence identity to the entire amino acid sequence of SEQ ID NO: 6.

6. The method according to claim 5, wherein the DNA comprises a c09478 gene having the sequence of SEQ ID NO: 5.

7. The method according to claim 1, wherein said bacterium has been further modified to express a DNA encoding the protein of SEQ ID NO: 2 or a protein having at least 95% sequence identity to the entire amino acid sequence of SEQ ID NO: 2.

8. The method according to claim 7, wherein the DNA comprises a c0011 gene having the sequence of SEQ ID NO: 1.

9. The method according to claim 5, wherein said bacterium has been further modified to express a DNA encoding the protein of SEQ ID NO: 2 or a protein having at least 95% sequence identity to the entire amino acid sequence of SEQ ID NO: 2.

10. The method according to claim 9, wherein the DNA comprises a c0011 gene having the sequence of SEQ ID NO: 1.

11. The method according claim 1, wherein the bacterium belongs to the genus *Escherichia.*

12. The method according to claim 11, wherein the bacterium is *Escherichia coli.*

13. The method according claim 1, wherein the bacterium belongs to the genus *Pantoea.*

14. The method according to claim 13, wherein the bacterium is *Pantoea ananatis.*

15. The method according to claim 1, wherein said L-amino acid is selected from the group consisting of an aromatic L-amino acid and a non-aromatic L-amino acid.

16. The method according to claim 15, wherein said aromatic L-amino acid is selected from the group consisting of L-phenylalanine, L-tyrosine, and L-tryptophan.

17. The method according to claim 15, wherein said non-aromatic L-amino acid is selected from the group consisting of L-threonine, L-lysine, L-cysteine and L-cysteine derivatives, L-methionine, L-leucine, L-isoleucine, L-valine, L-histidine, glycine, L-serine, L-alanine, L-asparagine, L-aspartic acid, L-glutamine, L-glutamic acid, L-proline, L-arginine and O-acetyl-L-serine.

18. The method according to claim 17, wherein said L-amino acid is selected from the group consisting of L-cysteine, L-valine, L-leucine, L-isoleucine, L-threonine, L-glutamic acid, glycine, L-alanine, L-histidine, and O-acetyl-Lserine.

* * * * *